United States Patent
Zhi

(10) Patent No.: US 12,110,308 B2
(45) Date of Patent: Oct. 8, 2024

(54) PHOSPHOR(N)AMIDATACETAL AND PHOSPH(ON)ATALCETAL COMPOUNDS

(71) Applicant: NUCORION PHARMACEUTICALS, INC., San Diego, CA (US)

(72) Inventor: Lin Zhi, San Diego, CA (US)

(73) Assignee: NUCORION PHARMACEUTICALS, INC., San Diego, CA (US)

(*) Notice: Subject to any disclaimer, the term of this patent is extended or adjusted under 35 U.S.C. 154(b) by 1097 days.

(21) Appl. No.: 16/960,819

(22) PCT Filed: Jan. 8, 2019

(86) PCT No.: PCT/US2019/012765
§ 371 (c)(1),
(2) Date: Oct. 8, 2020

(87) PCT Pub. No.: WO2019/139920
PCT Pub. Date: Jul. 18, 2019

(65) Prior Publication Data
US 2021/0188887 A1    Jun. 24, 2021

Related U.S. Application Data

(60) Provisional application No. 62/615,851, filed on Jan. 10, 2018.

(51) Int. Cl.

| C07F 9/6561 | (2006.01) |
|---|---|
| A61K 31/4162 | (2006.01) |
| A61K 31/4178 | (2006.01) |
| A61K 31/44 | (2006.01) |
| A61K 31/47 | (2006.01) |
| A61K 31/4709 | (2006.01) |
| A61K 31/513 | (2006.01) |
| A61K 31/5377 | (2006.01) |
| A61K 31/675 | (2006.01) |
| A61K 31/7052 | (2006.01) |
| A61K 31/7056 | (2006.01) |
| A61K 31/7076 | (2006.01) |
| A61K 38/21 | (2006.01) |
| A61K 45/06 | (2006.01) |
| A61P 1/16 | (2006.01) |

(52) U.S. Cl.
CPC ...... *C07F 9/65616* (2013.01); *A61K 31/4178* (2013.01); *A61K 31/44* (2013.01); *A61K 31/47* (2013.01); *A61K 31/4709* (2013.01); *A61K 31/513* (2013.01); *A61K 31/5377* (2013.01); *A61K 31/675* (2013.01); *A61K 31/7056* (2013.01); *A61K 38/212* (2013.01); *A61K 45/06* (2013.01); *A61P 1/16* (2018.01); *A61K 31/4162* (2013.01); *A61K 31/7052* (2013.01); *A61K 31/7076* (2013.01)

(58) Field of Classification Search
CPC ...... C07F 9/65616; A61P 1/16; A61K 31/675; A61K 31/7056; A61K 31/4162; A61K 31/7052
See application file for complete search history.

(56) References Cited

U.S. PATENT DOCUMENTS

| 4,401,808 | A | 8/1983 | Yamaji et al. |
|---|---|---|---|
| 4,689,404 | A | 8/1987 | Kawada et al. |
| 4,692,434 | A | 9/1987 | Hertel |
| 4,966,891 | A | 10/1990 | Morio et al. |
| 5,476,932 | A | 12/1995 | Brinkman et al. |
| 6,312,662 | B1 | 11/2001 | Erion et al. |
| 7,456,155 | B2 | 11/2008 | Sommadossi et al. |
| 8,097,706 | B2 | 1/2012 | Lee et al. |
| 8,603,999 | B2 | 12/2013 | Drummond et al. |
| 8,653,048 | B2 | 2/2014 | Xue et al. |
| 8,741,858 | B2 | 6/2014 | Ren et al. |
| 9,447,137 | B2 | 9/2016 | Suo |
| 9,744,186 | B2 | 8/2017 | Suo |
| 10,000,521 | B2 | 6/2018 | Suo et al. |
| 10,059,733 | B2 | 8/2018 | Suo et al. |
| 10,435,429 | B2 | 4/2019 | Zhi |
| 10,899,786 | B2 | 1/2021 | Cai et al. |
| 2009/0069557 | A1 | 3/2009 | Palle et al. |
| 2009/0221524 | A1 | 9/2009 | Kotra et al. |
| 2010/0075917 | A1 | 3/2010 | Decout et al. |
| 2010/0081628 | A1 | 4/2010 | Du et al. |

(Continued)

FOREIGN PATENT DOCUMENTS

| CN | 1033183 | 5/1989 |
|---|---|---|
| CN | 101525361 | 9/2009 |

(Continued)

OTHER PUBLICATIONS

Broeders et al., 1990, A 400- and 600-MHz 'H NMR conformation study on nucleoside cyclic 3',5' Pv-TPB systems. Conformation transmission induces diequatorial orientation of the 3',5'-dioxaphosphoarinane ring in a nonchair conformation, J> Am. Chem. Soc, 112:7475-7482.

Du et al., Sep. 2012, β-D-2'-α-F-2'-β-C Methyl-6-O-substituted 3',5'-cyclic phosphate nucleotide prodrugs as inhibitors of hepatitis C virus replication: A structure-activity relationship study, Bioorganic & Medicinal Chemistry Letters, 22(18):5924-5929.

(Continued)

*Primary Examiner* — Andrew D Kosar
*Assistant Examiner* — John D McAnany
(74) *Attorney, Agent, or Firm* — Knobbe, Martens, Olson & Bear, LLP

(57) ABSTRACT

Provided herein are phosphor (n) amidatacetal and phosph (on) atacetal compounds, their preparation and their uses, such as treating liver diseases or nonliver diseases via intervening in the molecular pathways in the liver. These compounds may be effective in the treatment of hepatitis or other viral infections either alone or in combination with one or more additional therapeutic agents.

24 Claims, No Drawings

(56) References Cited

U.S. PATENT DOCUMENTS

| | | |
|---|---|---|
| 2010/0286084 A1 | 11/2010 | Ren et al. |
| 2011/0183933 A1 | 7/2011 | Guzi et al. |
| 2012/0009147 A1 | 1/2012 | Cho et al. |
| 2012/0070411 A1 | 3/2012 | Beigelman et al. |
| 2012/0088908 A1 | 4/2012 | Xue et al. |
| 2015/0224208 A1 | 8/2015 | Ueki et al. |
| 2017/0057981 A1 | 3/2017 | Chen et al. |
| 2018/0044368 A1 | 2/2018 | Zhi |
| 2019/0100551 A1 | 4/2019 | Zhi |
| 2020/0399227 A1 | 12/2020 | Zhi |
| 2022/0220145 A1 | 7/2022 | Zhi |
| 2022/0298198 A1 | 9/2022 | Zhi |
| 2022/0298199 A1 | 9/2022 | Zhi |
| 2023/0159574 A1 | 5/2023 | Zhi |
| 2023/0391807 A1 | 12/2023 | Zhi |

FOREIGN PATENT DOCUMENTS

| | | |
|---|---|---|
| CN | 101875680 | 11/2010 |
| CN | 101921303 | 12/2010 |
| CN | 102219817 | 10/2011 |
| CN | 106317116 | 1/2017 |
| CN | 106554382 | 4/2017 |
| CN | 108350016 | 7/2018 |
| CN | 113906040 | 1/2022 |
| EA | 201100850 | 3/2012 |
| EA | 27929 B1 | 9/2017 |
| EP | 0 588 317 | 3/1994 |
| EP | 0 602 454 B1 | 4/1996 |
| EP | 2 423 215 | 2/2012 |
| EP | 2 615 101 | 7/2013 |
| EP | 1 301 519 | 2/2015 |
| JP | 2005-525991 | 9/2005 |
| WO | WO 82/000293 | 2/1982 |
| WO | WO 02/008241 | 1/2002 |
| WO | WO 02/12242 | 2/2002 |
| WO | WO 05/018330 | 3/2005 |
| WO | WO 06/065525 | 6/2006 |
| WO | WO 07/022073 | 2/2007 |
| WO | WO 08/005555 | 1/2008 |
| WO | WO 08/030373 | 3/2008 |
| WO | WO 08/083465 | 7/2008 |
| WO | WO 08/144980 | 12/2008 |
| WO | WO 09/082846 | 7/2009 |
| WO | WO 09/106243 | 9/2009 |
| WO | WO 09/152095 | 12/2009 |
| WO | WO 10/027326 | 3/2010 |
| WO | WO 10/056403 | 5/2010 |
| WO | WO 10/130726 | 11/2010 |
| WO | WO 11/130557 | 10/2011 |
| WO | WO 12/031539 | 3/2012 |
| WO | WO 12/040126 | 3/2012 |
| WO | WO 12/078416 | 6/2012 |
| WO | WO 13/142525 | 9/2013 |
| WO | WO 13/177195 | 11/2013 |
| WO | WO 14/032481 | 3/2014 |
| WO | WO 14/043380 | 3/2014 |
| WO | WO 14/068265 | 5/2014 |
| WO | WO 14/074725 | 5/2014 |
| WO | WO 1234567 | 6/2014 |
| WO | WO 14/124430 | 8/2014 |
| WO | WO 14/145207 | 9/2014 |
| WO | WO 14/204831 | 12/2014 |
| WO | WO 15/081133 | 6/2015 |
| WO | WO 15/134334 | 9/2015 |
| WO | WO 15/181624 | 12/2015 |
| WO | WO 16/138026 | 9/2016 |
| WO | WO 17/223020 | 12/2017 |
| WO | WO 17/223421 | 12/2017 |
| WO | WO 18/091542 | 5/2018 |
| WO | WO 18/113652 | 6/2018 |
| WO | WO 19/027905 | 2/2019 |
| WO | WO 19/120299 | 6/2019 |
| WO | WO 19/139920 | 7/2019 |
| WO | WO 19/143860 | 7/2019 |
| WO | WO 19/169323 | 9/2019 |
| WO | WO 20/154917 | 8/2020 |
| WO | WO 20/219464 | 10/2020 |
| WO | WO 22/086858 | 4/2022 |

OTHER PUBLICATIONS

Gillen et al., 1976, Some biochemical properties of alkyl phosphotriesters of cyclic AMP, Biochemical and Biophysical Research Communications, 68(3):836-840.

Kataoka et al., 1986, A simple synthesis of adenosine 3',5'-cyclic phosphate alkyl triesters, Chemistry Letters, pp. 1221-1224.

Nagyvary et al., 1973, Studies on neutral esters of cyclic AMP, Biochemical and Biophysical Research Communications, 55(4):1072-1077.

Ogilvie et al., 1978, The alkylation of purines, pyrimidines and nucleotides by dialkyl sulfates with tetrabutylammonium fluoride, Tetrahedron Letters, 35:3203-3206.

Reddy et al., Oct. 8, 2010, 2'-Deoxy-2'-α-fluoro-2'-β-methyl 3',5'-cyclic phosphate nucleotide prodrug analogs as inhibitors of HCV NS5B polymerase: discovery of PSA-352938, Bioorganic & Medicinal Chemistry Letters, 29(48):7376-7380.

Van Pelt et al., Dec. 5, 1986, Gentamicin nucleotidyltransferase, The Journal of Biological Chemistry, 261(34):15995-15999.

Almarsson et al., "Crystal Engineering of the Composition of Pharmaceutical Phases. Do Pharmaceutical Co-crystals Represent a New Path to Improved Medicines?" The Royal Society of Chemistry (2004) 1889-1896.

Bentrude et al., "Efficient Preparation of Cycle 3',5'-Phosphoramidates and Amidates of Antiviral and Antitumor 5-X-2'-Deoxyuridines (X=H, CH3, I, F, CF3, trans-CH=CHBr)," Nucleosides and Nucleotides (1989) vol. 8, No. 7, pp. 1359-1367.

Beres et al., "An Efficient Synthesis of Certain 5-Substituted-2'-Deoxyuridine 3',5'-Cyclic Monophosphate P-O-Alkyl_Aralkyl) Esters. The Crystal and Molecular Structure of 5-Iodo-2'-Deoxyuridine 3',5'-Cyclic Monophosphate P-O-methyl Ester with Axial Methoxy Group, " Tetrahedron (1984) vol. 40, No. 12, pp. 2405-2414.

Chen et al., "A Facile One-Pot Synthesis of N4-Alkyloxycarbonyl Cytosine Nucleosides," Synthetic Communications (2004) vol. 34, No. 18, pp. 3273-3279.

Cheng et al., "QSAR Models for Phosphoramidate Prodrugs of 2'-Methylcytidine as Inhibitors of Hepatitis C Virus Based on PSO Boosting," Chem Biol and Drug Design (2011) 78:948-959.

Chou et al., "Analysis of combined drug effects: a new look at a very old problem." Trends Pharmacol Sci (1983) 4:450-454.

Chou et al., "Quantitative analysis of dose-effect relationships: the combined effects of multiple drugs or enzyme inhibitors." Adv Enzyme Regul (1984) 22:27-55.

Chou, T.C., "Theoretical basis, experimental design, and computerized simulation of synergism and antagonism in drug combination studies," Pharmacol Rev. (2006) 58(3):621-81.

Crook et al., "Examining the origin of selectivity in the reaction of racemic alcohols with chiral N-phosphoryl oxazolidinones," (2014) 25:1298-1308.

Dewaziers et al., "Cytochrome P450 Isoenzymes, Epoxide Hydrolase and Glutathione Transferases in Rat and Human Hepatic and Extraheptaic Tissues," J Pharmacol and Experimental Therapeutics (1990) vol. 253, No. 1, pp. 387-394.

Donghi et al., "Synthesis and evaluation of novel phosphoramidate prodrugs of 2'-methyl cytidine as inhibitors of hepatitis c virus NS5B polymerase," Bioorganic & Medicinal Chem Letters (2009) 19:1392-1395.

Griffiths, 2001, Cytomegalovirus, in Principles and Practice of Clinical Virology, A.J. Zuckerman et al., eds, 5th ed., pp. 85-122.

Imai et al., "Novel cell-based reporter assay system using epitope-tagged protein for the identification of agonistic ligands of constitutive androstane receptor (CAR)," Drug Metab and Phamaco (2013) 28(4):290-298.

Jain et al., "Synthesis and Study of Cyclic Pronucleotides of 5-fluoro-2'-deoxyuridine," Bioorganic and Med Chem Letters (2012) vol. 22, pp. 4497-4501.

Kawaguchi et al., "Specificity of Esterases and Structure of Prodrug Esters. II. Hydrolytic Regeneration Behavior of 5-Fluro-2'-

(56) References Cited

OTHER PUBLICATIONS deoxyuridine (FUdR) from 3',5'-Diesters of FUdR with Rat Tissue Homogonates and Plasmain Relation to Their Antitumor Activity," Chem and Pharma Bulletin (1985) vol. 33, No. 4, pp. 1652-1659.

Kotra et al., "Structure-Activity Relationships of 2'-Deoxy-2',2'difluoro-L-erythro-pentofuranosyl Nucleosides," J Med Chem (1997) 40(1):3635-3644.

Kroep et al., "Pretreatment Deoxycytidine Kinase Levels Predict in Vivo Gemcitabine Sensitivity," Mol. Cancer Ther. (2002) 1, 371-376.

LaMarche et al., Oct. 2012, Anti-hepatitis C virus activity and toxicity of type III phosphatidylinositol-4-kinase beta inhibitors, Antimicrobial Agents and Chemotherapy, 56(10): 5149-5156.

Lianzhi et al., "Synthesis of Acyclonucleoside Derivatives and Analogues of 5-Fluorouracil," Nanjing Yaoxueyuan Xuebao (19896) vol. 17, No. 3, pp. 161-166.

Lohman et al., "Inactivation of lactobacillus leichmannii ribonucleotide reductase by 2',2'-difluoro-2'-deoxycitifdine 5'-triphosphate: Covalent Modification," Biochem (2010) 49(7):1404-1417.

Mackman et al., "Discovery of GS-9131: Design, synthesis and optimization of amidate prodrugs of the novel nucleoside phosphonate HIV reverse transcriptase (RT) inhibitor GS-9148," Bioorganic & Medicinal Chemistry (2010) 18:3606-3617.

Muller et al., Antiviral Strategies, 24 pp., 4 (H.-G. Krausslich et al., eds., 2009).

Pubchem SCHEMBLCN285547, CID: 53839260, Create Date: Dec. 4, 2011, 11 pages.

Quintiliani et al., "Design, synthesis and biological evaluation of 2'-deoxy-2',2'-diflouro-5-halouridine phosphoramidate protides," Bioorganic & Medicinal Chemistry (2011) 19(14):4338-4345.

Rautio et al., "Prodrugs: design and clinical applications," Nature Reviews Drug Discovery (2008) 7:255-270.

Saiki et al. "DCK is frequently inactivated in acquired gemcitabine-resistant human cancer cells," Biochim. Biophys. Res. Commun. (2012) 421, 98-104.

Slusarczyk et al., "Application of ProTide Technology to Gemcitabine: A Successful Approach to Overcome the Key Cancer Resistance Mechanisms Leads to a New Agent (NUC-1031) in Clinical Development," J. Med. Chem. (2014) vol. 57, pp. 1531-1542.

Tanaka et al., "Chemical Synthesis of Deosyribonucleotide with a 5'-Phosphoryl Group on a Polystyrene Polymer Support by the Phosphotriester Method," Chem and Pharma Bulletin (1987) 35:2726-2733.

Thornton et al., "Nucleoside Phosphate and Phosphonate Prodrug Clinical Candidates," Journal of Medicinal Chemistry (2016) 59:10400-10410.

Wilson et al., "Precursor synthesis towards the development of [1241]-labelled 2',2'-difluoro-2'deoxycytidine as a potential pet radiotracer for the anticancer drig gemicitabine," J Labelled Compounds and Radiopharmaceuticals (2001) 44(S1):S976-978.

Wu et al., "Synthesis and Biological Activity of a Gemcitabine Phosphoramidate Prodrug," J. Med Chem (2007) 50(15):3743-3746.

Zhao et al., "Synthesis and Biological Evaluation of Oral Prodrugs Based on the Structure of Gemcitabine," Chem Bio & Drug Des (2012) 80(3):479-488.

Zhuk, R., "Structure-Activity Relationship in Ftorafur (Tegafur) and Related 5-FU Prodrugs," Advances in Experimental and Biology (Purine and Pyrimidine Metabolism in Man IW) (1998) pp. 677-680.

International Search Report and Written Opinion dated Mar. 27, 2019 in PCT/US2019/012765.

Beres et al., 1986, Synthesis and antitumor and antiviral properties of 5-halo- and 5-(trifluoromethyl)-2'-deoxyuridine 3',5'-cyclic monophosphates and neutral triesters, J. Med. Chem., 29:1243-1249.

Shestakova. 2015, Antiviral drugs, Journal for continuous medical education of physicians, Infectious Diseases: news, opinions, training, 1(10):77-86.

Tanaka et al., 1986, Trityloxyethylamino group for the protection of phosphoryl group in oligonucleotide synthesis, Tetrahedron Letters, 27(46):5641-5644.

Package insert for Fluorouracil injection, for intravenous use, Spectrum Pharmaceuticals, Inc., Revised Jul. 2016.

PHOSPHOR(N)AMIDATACETAL AND PHOSPH(ON)ATALCETAL COMPOUNDS

CROSS REFERENCE TO RELATED APPLICATIONS

This application is a U.S. National Phase of International Application No. PCT/US2019/012765, filed on Jan. 8, 2019 and published on Jul. 18, 2019 as WO 2019/0139920, which claims the benefit of U.S. Provisional Application No. 62/615,851 filed Jan. 10, 2018 entitled "PHOSPHOR (N) AMIDATACETAL AND PHOSPH (ON) ATALCETAL COMPOUNDS", which is incorporated by reference in its entirety.

FIELD

The present disclosure relates to the field of chemistry and medicine. More specifically, the present disclosure relates to phosphor(n)amidatacetal and phosph(on)atalcetal compounds, their preparation and their uses. In some embodiments, such compounds are useful to selectively deliver certain nucleotides to the liver.

BACKGROUND

The following description of the background is provided to aid in understanding the invention, but is not admitted to be, or to describe, prior art to the invention.

Natural nucleos(t)ide compounds are essential molecular building blocks of life and many nucleos(t)ide analog compounds are widely used as antiviral and anticancer agents. Due to the poor lipophilic nature, nucleos(t)ide analog compounds are rarely used as an oral agent. Nucleos(t)ide analog compounds may be used in a form to enhance their oral absorption (e.g., See P. J. Thornton, et al. Journal of Medicinal Chemistry 59:10400-10410 (2016) and J. Rautio, et al. Nature Reviews Drug Discovery 7:255-270 (2008)).

Despite the known nucleos(t)ide analog compounds, there is a need for new compounds with favorable physicochemical, biopharmaceutical or pharmacokinetic properties. For example, liver-targeting compounds which are not active outside the liver reducing pharmacological or toxicological effects of a biologically active agent outside the target tissue. Thus, there is a need for improved liver-targeting compounds in which the compounds remain relatively non-cytotoxic outside the liver.

SUMMARY

Novel phosphor(n)amidatacetal and phosph(on)atalcetal compounds of nucleos(t)ides, their preparation and their uses are described. Some embodiments are related to novel phosphor(n)amidatacetal and phosph(on)atalcetal compounds that are absorbed in the intestine and taken up via the hepatic portal vein to the liver where the compounds provide a therapeutic benefit. Another aspect includes the use of phosphor(n)amidatacetal and phosph(on)atalcetal compounds to treat diseases that benefit from enhanced drug distribution to the liver and like tissues and cells, including but not limited to hepatitis, cancer, liver fibrosis, fatty liver, and metabolic, and cardiovascular diseases where the liver is involved in the production and/or the homeostasis control of the biochemical end products, e.g. glucose, cholesterol, fatty acids, triglycerides, lipoproteins, and apolipoproteins. In another aspect, phosphor(n)amidatacetal and phosph(on)atacetal compounds are used to increase the pharmacological or clinical activity of certain nucleos(t)ide analog compounds. In another aspect, phosphor(n)amidatacetal and phosph(on)atacetal compounds are used to reduce potential side effects of certain nucleos(t)ide analog compounds, especially the side effects occurring outside the liver. In some embodiments, the phosphor(n)amidatacetal and phosph(on)atacetal compounds are useful in the delivery of diagnostic imaging agents to the liver. Some additional embodiments relate to a method of making phosphor(n)amidatacetal and phosph(on)atacetal compounds.

Some embodiments provided herein include a compound of Formula I:

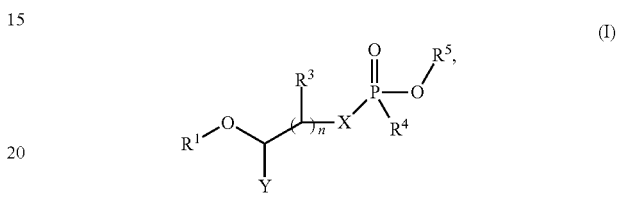

or a stereoisomer or a pharmaceutically acceptable salt thereof, wherein $R^1$, $R^3$, $R^4$, $R^5$, X, Y and n have any of the values described herein.

In some embodiments, $R^4$ is the $R^4$ portion of a monophosphate or monophosphonate therapeutic agent having the structure:

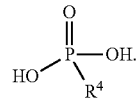

In some embodiments, $R^4$ comprises a nucleoside, or amide or ester thereof. In some embodiments, $R^4$ comprises a nucleoside, or nucleoside analog. In some embodiments, $R^4$ comprises a ribonucleoside, deoxyribonucleoside or amide or ester thereof. In some embodiments, $R^4$ comprises a ribonucleoside, ribonucleoside analog, deoxyribonucleoside, deoxyribonucleoside analog or amide or ester thereof. In some embodiments, $R^4$ comprises a natural ribonucleoside, natural deoxyribonucleoside, unnatural ribonucleoside, unnatural deoxyribonucleoside, or amide or ester thereof. In some embodiments, $R^4$ comprises a nucleobase, or amide thereof. In some embodiments, $R^4$ comprises a nucleobase analog, or amide thereof. In some embodiments, $R^4$ comprises a purine nucleobase, pyrimidine nucleobase or amide thereof. In some embodiments, $R^4$ comprises a purine nucleobase analog, pyrimidine nucleobase analog or amide or ester thereof. In some embodiments, $R^4$ comprises a natural or unnatural nucleobase or amide thereof. In some embodiments, $R^4$ comprises a substituted tetrahydrofuran. In some embodiments, $R^4$ comprises a tetrahydrofuran substituted with one to four $R^{1A}$ where one $R^{1A}$ is a nucleobase, or amide thereof. In some embodiments, $R^4$ comprises a tetrahydrofuran substituted with one to four $R^{1A}$ where one $R^{1A}$ is a nucleobase analog, or amide thereof. In some embodiments, $R^4$ comprises a tetrahydrofuran substituted with one to four $R^{1A}$ where one $R^{1A}$ is a purine nucleobase, pyrimidine nucleobase or amide thereof. In some embodiments, $R^4$ comprises a tetrahydrofuran substituted with one to four $R^{1A}$ where one $R^{1A}$ is a purine nucleobase analog, pyrimidine nucleobase analog or amide or ester thereof. In some embodiments, $R^4$ comprises a tetrahydrofuran substituted with one to four $R^{1A}$ where one $R^{1A}$ is a natural or unnatural nucleobase or amide thereof.

Some embodiments relate to a compound of Formula II, III, IV, V, and VI:

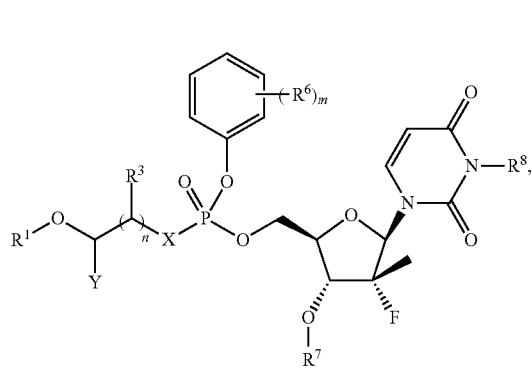

(II)

or a stereoisomer or a pharmaceutically acceptable salt thereof,

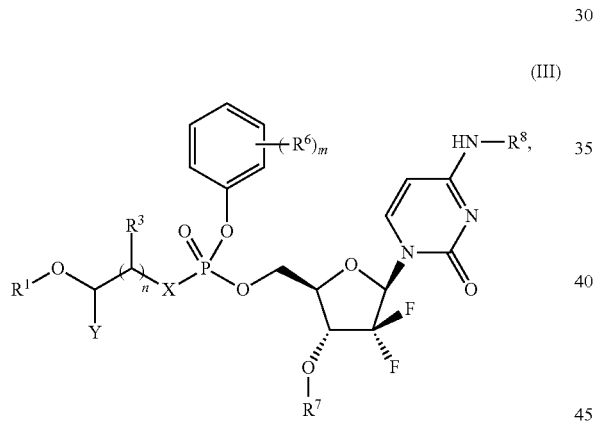

(III)

or a stereoisomer or a pharmaceutically acceptable salt thereof,

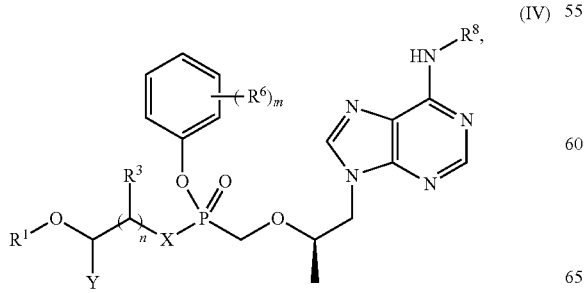

(IV)

or a stereoisomer or a pharmaceutically acceptable salt thereof,

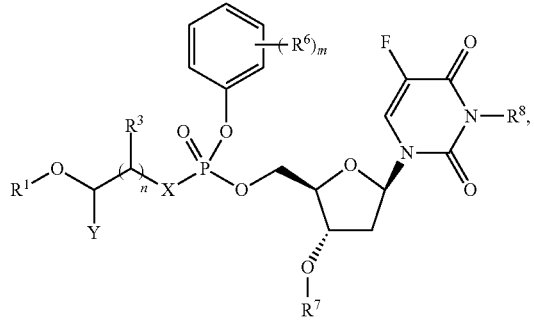

(V)

or a stereoisomer or a pharmaceutically acceptable salt thereof,

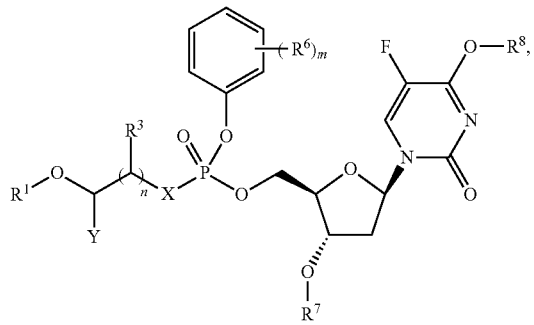

(VI)

or a stereoisomer or a pharmaceutically acceptable salt thereof, wherein $R^1$, $R^3$, $R^4$, $R^5$, $R^6$, $R^7$, $R^8$, X, Y, m and n have any of the values described herein.

Some embodiments relate to a compound of Formula Ia, IIa, IIIa, IVa, Va, and VIa:

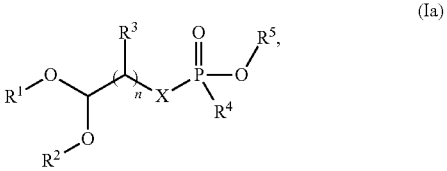

(Ia)

or a stereoisomer or a pharmaceutically acceptable salt thereof,

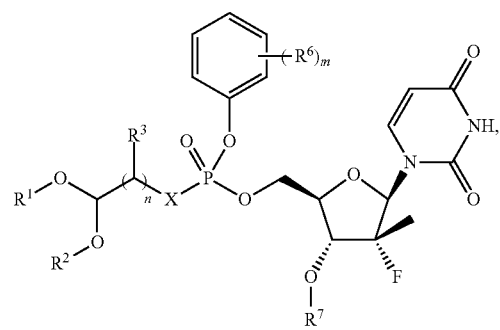
(IIa)

or a stereoisomer or a pharmaceutically acceptable salt thereof,

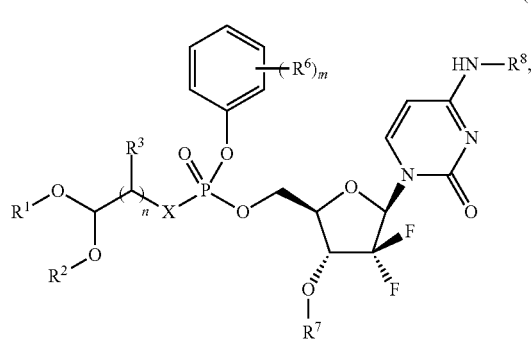
(IIIa)

or a stereoisomer or a pharmaceutically acceptable salt thereof,

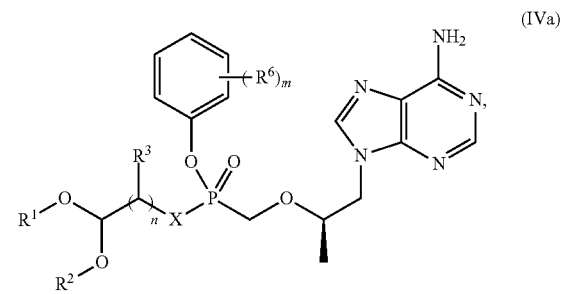
(IVa)

or a stereoisomer or a pharmaceutically acceptable salt thereof,

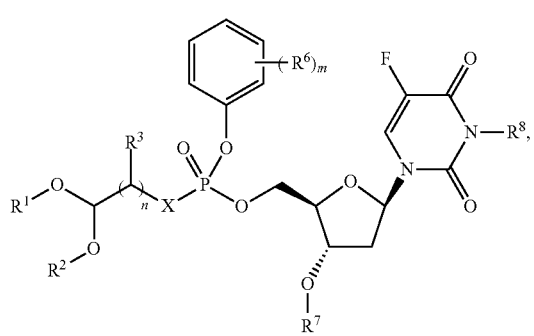
(Va)

or a stereoisomer or a pharmaceutically acceptable salt thereof,

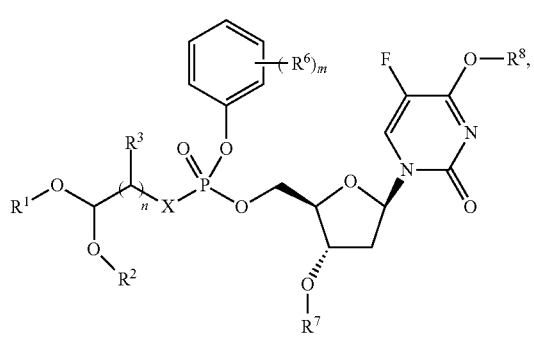
(VIa)

or a stereoisomer or a pharmaceutically acceptable salt thereof, or a stereoisomer or a pharmaceutically acceptable salt thereof, wherein $R^1$, $R^2$, $R^3$, $R^4$, $R^5$, $R^6$, $R^7$, $R^8$, X, m and n have any of the values described herein.

Some embodiments relate to a pharmaceutical composition comprising any of the above compounds and a pharmaceutically acceptable excipient.

Some embodiments relate to a method of treating a disease, disorder or condition comprising administering an effective amount of any of the above compounds.

In some embodiments, the disease, disorder or condition is a disease, disorder or condition of the liver.

In some embodiments, the disease, disorder or condition is a metabolic, cardiovascular or hormonal disease in which the liver is involved in the production and/or the homeostasis control of the biochemical end products of the disease, disorder or condition.

In some embodiments, the disease, disorder or condition is selected from the group consisting of hepatitis, cancer, liver fibrosis, fatty liver, malaria, viral infection, parasitic infection, diabetes, hyperlipidemia, atherosclerosis, obesity, dyslipidemia, hyperglycemia and a hormonal condition.

In some embodiments, the non-liver disease, disorder or condition is a viral infection, cancer, or other disease in which the phosphor(n)amidatacetal and phosph(on)atacetal compounds enhances the distribution of an active drug to the target tissue or cell.

Some embodiments relate to a method of treating a liver disease comprising administering an effective amount of a compound of any of the above compounds to a subject in need thereof, wherein $R^4$ is a nucleoside or a nucleoside equivalent antiviral or anticancer agent.

Some embodiments further comprise administering an effective amount of at least one additional therapeutic agent to the subject in need thereof.

Some embodiments relate to a method of delivering a diagnostic imaging agent to the liver of a subject in need thereof, comprising administering to the subject an effective amount of any of the above compounds.

In some embodiments, the subject is a mammal.
In some embodiments, the subject is human.
Some embodiments relate to a method of inhibiting viral replication in a cell comprising contacting the cell with any of the above compounds.

Some embodiments relate to a method of intervening in a molecular pathway or modulating a target in a cell comprising contacting the cell with any of the above compounds.

In some embodiments, the cell is in vivo.
In some embodiments, the cell is ex vivo.
In some embodiments, the cell is a hepatocyte.
In some embodiments, the cell is mammalian.
In some embodiments, the cell is human.
Some embodiments of the compounds, compositions, and methods provided herein include a pharmaceutical composition comprising any of the compounds provided herein and a pharmaceutically acceptable excipient.

Some embodiments of the compounds, compositions, and methods provided herein include a method of treating a disease or condition in the liver in a subject comprising administering an effective amount of any of the compounds provided herein to a subject in need thereof.

Some embodiments provided herein include a method of treating a disease or condition by intervening in a molecular pathway/target (e.g. a receptor or an enzyme or the like) in the liver in a subject comprising administering an effective amount of any prodrug compounds of fatty acids that are absorbed via the hepatic portal vein to the liver to a subject in need thereof.

Some embodiments also include administering an effective amount of one or more additional therapeutic agents to the subject in need thereof.

In some embodiments, the subject is a mammal.
In some embodiments, the subject is a human.
Some embodiments also include the use of any one of the compounds provided herein in combination with an additional therapeutic agent.

Some embodiments of the compounds, compositions, and methods provided herein include any one of the compositions provided herein for use in the preparation of a medicament for treating a disease or condition in the liver or a disease or condition in which the physiological or pathogenic pathways involve the liver.

DETAILED DESCRIPTION

Nucleoside monophosphates and monophosphonates are attractive drug targets as conversion to the active triphosphate/phosphonodiphosphate is rapid and the initial rate limiting phosphorylation is not required. However, nucleoside monophosphates and monophosphonates are limited as drug candidates as they are not efficiently transported to therapeutic target in cells. Thus, strategies have been developed to facilitate delivery of nucleoside monophosphates and monophosphonates into cells. The nucleoside based drugs sofosbuvir, gemcitabine and oral tenofovir are approved to treat hepatitis C, cancer, hepatitis B and HIV, respectively. Table 1 provides the unmasked monophosphate of sofosbuvir and monophosphate of gemcitabine, and tenofovir an unmasked monophosphonate form. These compounds are known to undergo rapid phosphorylation to the active triphosphate/phosphonodiphosphate forms (e.g., See P. J. Thornton, et al. J. Med. Chem., (2016), 59(23):10400-10410).

TABLE 1

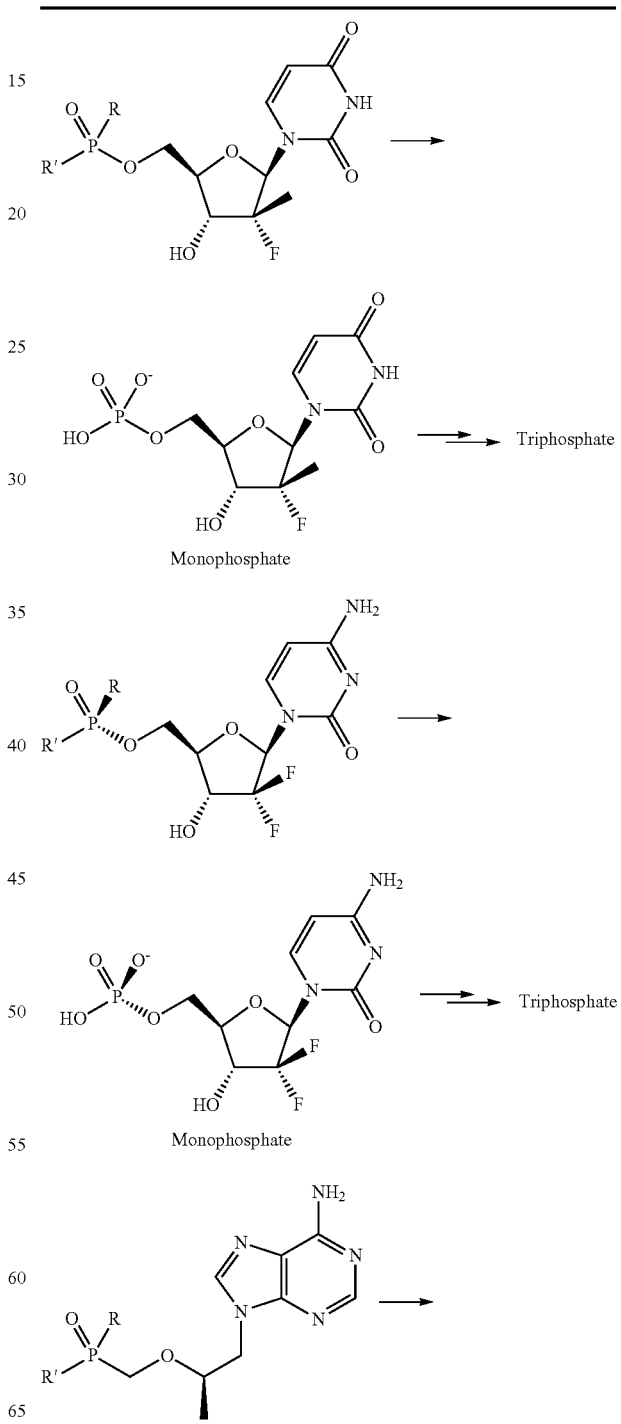

TABLE 1-continued

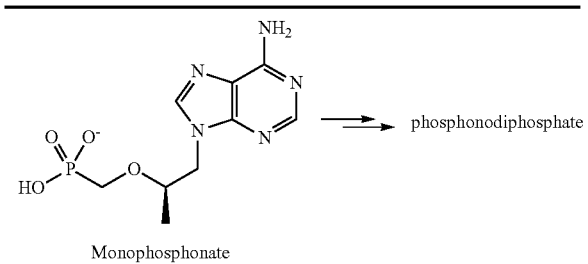

Monophosphonate → phosphonodiphosphate

The present embodiments are directed to compositions and methods related to novel phosphor(n)amidatacetal and phosph(on)atacetal compounds, their preparation and their uses. In some embodiments, the novel phosphor(n)amidatacetal and phosph(on)atacetal compounds facilitate delivery into cells of monophosphate and monophosphonate therapeutic agents, such as nucleoside monophosphates and monophosphonates. In some embodiments, the novel phosphor(n)amidatacetal and phosph(on)atacetal compounds facilitate delivery of the unmasked monophosphate of sofosbuvir, monophosphate of gemcitabine, or tenofovir into cells.

These phosphor(n)amidatacetal and phosph(on)atacetal compounds and their stereoisomers and pharmaceutically acceptable salts are represented by Formula I, II, III, IV, V and VI:

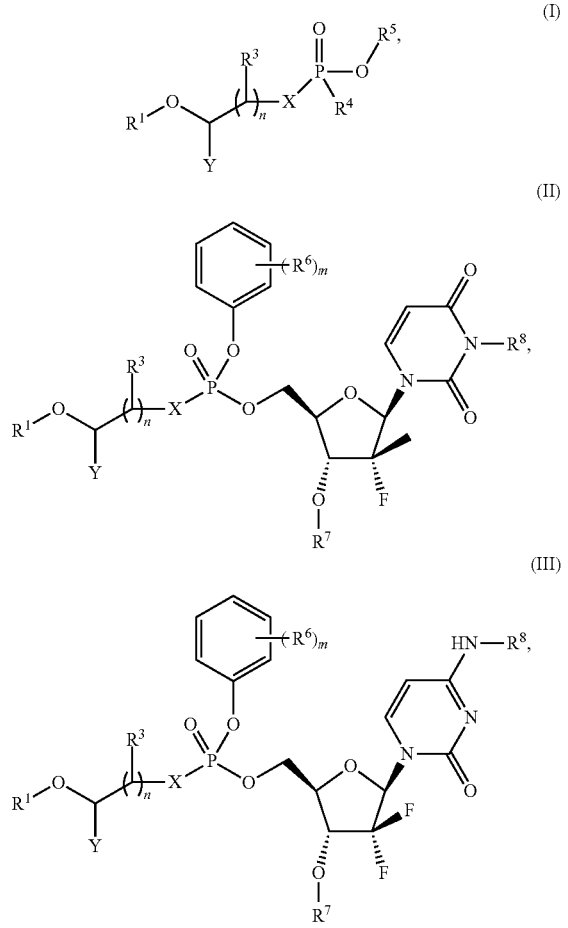

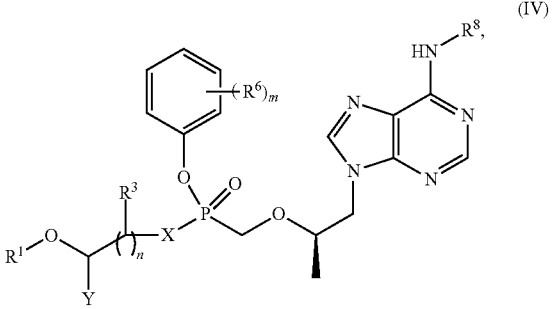

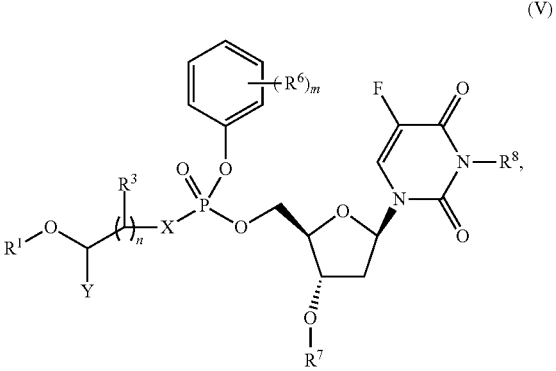

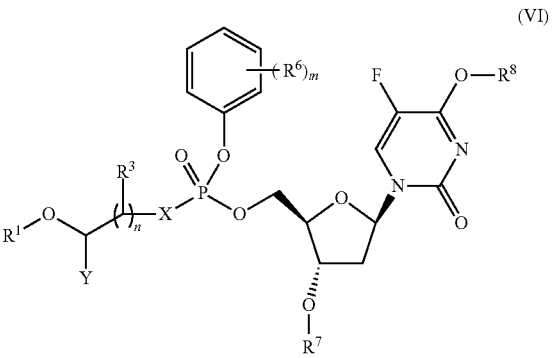

wherein $R^1$, $R^3$, $R^4$, $R^5$, $R^6$, $R^7$, $R^8$, X, Y, m and n have any of the values described herein.

In some embodiments, Y is $OR^2$ or H (hydrogen). In some embodiments, $R^1$ and $R^2$ are independently selected from the group consisting of an optionally substituted $C_1$-$C_6$ alkyl, an optionally substituted $C_{6-10}$ aryl, and an optionally substituted 5-10 membered heteroaryl, or alternatively $R^1$ and $R^2$ together with the atoms to which they are attached form a four to ten membered heterocycle optionally substituted with a $C_1$-$C_6$ alkyl. In some embodiments, Y is $OR^2$, and $R^1$ and $R^2$ are independently selected from the group consisting of an optionally substituted $C_1$-$C_6$ alkyl, an optionally substituted aryl, and an optionally substituted heteroaryl. In some embodiments, Y is $OR^2$, and $R^1$ and $R^2$ together with the atoms to which they are attached form a four to ten membered heterocycle optionally substituted with a $C_1$-$C_6$ alkyl. In some embodiments, Y is H (hydrogen), and $R^1$ is selected from the group consisting of hydrogen, an optionally substituted $C_1$-$C_6$ alkyl-C(O)—, an optionally substituted $C_1$-$C_6$ alkyl-$OCH_2$—, and an optionally substituted phenyl-$OCH_2$—.

In some embodiments, $R^3$ is selected from the group consisting of H, an optionally substituted $C_1$-$C_6$ alkyl, an optionally substituted arylalkyl, and an optionally substituted heteroarylalkyl.

In some embodiments, $R^4$ is a biological agent or part of a biological agent that is linked via a carbon or oxygen atom, such as a nucleoside or a nucleoside analog. In some embodiments, $R^4$ is the $R^4$ portion of a monophosphate or monophosphonate therapeutic agent having the structure:

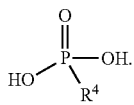

For example, in Cidofovir, $R^4$ is

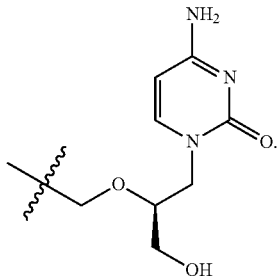 [SMILES: *CO[C@H](CO)Cn1ccc(N)nc1=O]

In PMEA, $R^4$ is

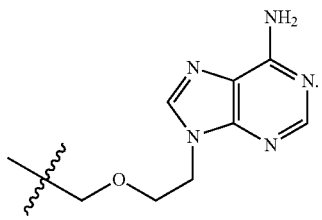 [SMILES: *COCCn1cnc2c(N)ncnc21]

In some embodiments, $R^5$ is an optionally substituted aryl.

In some embodiments, $R^6$ is independently selected from a group of halogen, an optionally substituted $C_1$-$C_6$ alkyl, and an optionally substituted $C_1$-$C_6$ alkyloxy.

In some embodiments, $R^7$ and $R^8$ are independently selected from the group consisting of H, an optionally substituted $C_1$-$C_6$ acyl, an optionally substituted $C_1$-$C_6$ alkyloxycarbonyl; and an optionally substituted $C_1$-$C_6$ carbamoyl.

In some embodiments, X is O or $NR^9$.

In some embodiments, $R^9$ is selected from the group consisting of H (hydrogen), an optionally substituted $C_1$-$C_6$ alkyl-$OCH_2$—, and an optionally substituted phenyl-$OCH_2$—, or alternatively, $R^9$ and $R^1$ together with the atoms to which they are attached form a five-member heterocycle.

In some embodiments, X is O or NH.

In some embodiments, n is 1 or 2.

In some embodiments, m is 0, 1, 2, or 3.

In some embodiments, the phosphor(n)amidatacetal and phosph(on)atacetal compounds of Formula I, II, III, IV, V, and VI are substrates of liver enzymes such as cytochrome p450 isozymes CYP3As (a family of monooxygenase), dehydrogenases, esterases, and amidases CYP3A4 is expressed in the liver in a level much higher than other tissues (DeWaziers et al. J Pharm Exp Ther 253:387 (1990)). Phosphor(n)amidatacetal and phosph(on) atacetal compounds of Formula I, II, III, IV, V, and VI are predominantly activated via CYP3A4 in the liver. In some embodiments, the compounds of Formula I, II, III, IV, V, and VI have high efficiency in liver-targeting via selective delivery of biologically active agents to the liver. In some embodiments, the phosphor(n)amidatacetal and phosph(on) atacetal compounds are used to increase the therapeutic index of a drug, since the compounds of Formula I, II, III, IV, V, and VI may not be active or may be less active outside the liver.

In some embodiments, due to the liver-targeting nature of the phosphor(n)amidatacetal and phosph(on)atacetal compounds of Formula I, II, III, IV, V, and VI, the compounds are used to treat diseases that benefit from enhanced drug distribution to the liver and like tissues and cells, including but not limited to diseases in the liver, such as hepatitis, liver cancer, liver fibrosis, fatty liver, malaria, other viral and parasitic infections, and metabolic, cardiovascular, and/or hormonal diseases where the liver is involved in the production and/or the homeostasis control of biochemical end products, e.g. glucose (e.g. diabetes); cholesterol, fatty acids, bile acids, triglycerides (e.g. hyperlipidemia, atherosclerosis and obesity), lipoproteins, apolipoproteins, and sex hormone-binding globulin (SHBG).

In some embodiments, the disclosed compounds are used to improve pharmacokinetic properties such as prolonging half-life or enhancing absorption of a drug. In addition, the disclosed methodology can be used to achieve sustained delivery of an active therapeutic agent. Due to the pharmacokinetic property enhancement of the phosphor(n)amidatacetal and phosph(on)atacetal compounds of Formula I, II, III, IV, V, and VI, the compounds are used to treat diseases that benefit from enhanced drug properties, including but not limited to diseases such as HIV and cancer. In some embodiments, a method of making these compounds is described. In some embodiments, the compounds are also useful in the delivery of diagnostic imaging agents to the liver or other tissues.

Certain compounds of Formula I, II, III, IV, V, and V have asymmetric centers where the stereochemistry may be unspecified, and the diastereomeric mixtures of these compounds are included, as well as the individual stereoisomers when referring to a compound of Formula I, I, III, IV, V, and VI generally.

Some embodiments of the compounds, compositions and methods provided herein include a pharmaceutical composition comprising a compound provided herein and a pharmaceutically acceptable carrier.

Some embodiments also include administering an effective amount of a second or multiple therapeutic agents in combination with a compound provided herein to the subject in need thereof.

In some embodiments, the subject is mammalian.

In some embodiments, the subject is human.

Some embodiments of the compounds, compositions and methods provided herein include a method of testing a compound in a cell comprising contacting the cell with the disclosed compounds.

Some embodiments of the compounds, compositions and methods provided herein include use of a compound provided herein in the treatment of a disease in the liver.

Some embodiments include the use of a compound provided herein in combination with additional therapeutic agent(s) for the treatment of a disease in the liver.

Some embodiments of the compounds, compositions and methods provided herein include use of a compound provided herein in the treatment of a disease or condition by intervening in a molecular pathway in the liver.

Some embodiments include the use of a compound provided herein in combination with additional therapeutic agent(s) for the treatment of a disease or condition by intervening in a molecular pathway in the liver.

Some embodiments of the compounds, compositions and methods provided herein include use of a compound provided herein in the treatment of a non-liver disease such as HIV infection and cancer.

Some embodiments include the use of a compound provided herein in combination with additional therapeutic agent(s) for the treatment of a non-liver disease such as HIV infection and cancer.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Definitions

In accordance with the present disclosure and as used herein, the following terms are defined with the following meanings, unless explicitly stated otherwise. It is to be understood that both the foregoing general description and the following detailed description are exemplary and explanatory only and are not restrictive of the subject matter claimed. In this application, the use of the singular includes the plural unless specifically stated otherwise. In this application, the use of "or" means "and/or" unless stated otherwise. Furthermore, use of the term "including" as well as other forms, such as "includes," and "included" is not limiting.

As used herein, ranges and amounts can be expressed as "about" a particular value or range. "About" also includes the exact amount. Hence "about 10%" means "about 10%" and also "10%."

As used herein, "optional" or "optionally" means that the subsequently described event or circumstance does or does not occur, and that the description includes instances where the event or circumstance occurs and instances where it does not. For example, an optionally substituted group means that the group is unsubstituted or is substituted.

As used herein, the singular forms "a," "an" and "the" include plural referents unless the context clearly dictates otherwise. Thus, for example, reference to a composition comprising "a therapeutic agent" includes compositions with one or a plurality of therapeutic agents.

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, isopropyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_2$-$C_6$ alkenyl, $C_2$-$C_6$ alkynyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclyloxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), sulfhydryl (mercapto), halo($C_1$-$C_6$)alkyl (e.g., —$CF_3$), halo($C_1$-$C_6$)alkoxy (e.g., —$OCF_3$), $C_1$-$C_6$ alkylthio, arylthio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), amino, amino($C_1$-$C_6$)alkyl, nitro, 0-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "sulfonyl" group refers to an "—$SO_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "S-sulfonamido" group refers to a "—$SO_2NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-sulfonamido" group refers to a "—$N(R_A)SO_2R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "O-carbamyl" group refers to a "—OC(=O)$NR_AR_B$" group in which R and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-carbamyl" group refers to an "—$N(R_A)$C(=O) OR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "O-thiocarbamyl" group refers to a "—OC(=S)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-thiocarbamyl" group refers to an "—$N(R_A)$C(=S) OR_B$" group in which $R_A$ and $R_B$ are each independently selected from hydrogen, $C_{1-6}$ alkyl, $C_{2-6}$ alkenyl, $C_2$-6 alkynyl, $C_{3-7}$ carbocyclyl, $C_{6-10}$ aryl, 5-10 membered heteroaryl, and 3-10 membered heterocycyl, as defined herein.

A "C-amido" group refers to a "—C(=O)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein each optionally substituted with one or more substituents selected from the group consisting of —OH, $C_{1-6}$ alkyl, $C_{3-7}$ carbocyclyl, $C_{6-10}$ aryl, 5-10 membered heteroaryl, 3-10 membered heterocycyl, $C_{1-6}$ alkyl optionally substituted with $C_{1-6}$ alkoxy or —OH and $C_{1-6}$ alkoxy optionally substituted with $C_{1-6}$ alkoxy or —OH.

An "N-amido" group refers to a "—$N(R_A)$C(=O)$R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein each optionally substituted with one or more substituents selected from the group consisting of —OH, $C_{1-6}$ alkyl, $C_{3-7}$ carbocyclyl, $C_{6-10}$ aryl, 5-10 membered heteroaryl, 3-10 membered heterocycyl, $C_{1-6}$ alkyl optionally substituted with $C_{1-6}$ alkoxy or —OH and $C_{1-6}$ alkoxy optionally substituted with $C_{1-6}$ alkoxy or —OH.

An "amino" group refers to a "—$NR_AR_B$" group in which $R_A$ and $R_B$ are each independently selected from hydrogen, $C_{1-6}$ alkyl, $C_{2-6}$ alkenyl, $C_{2-4}$ alkynyl, $C_{3-7}$ carbocyclyl, $C_{6-10}$ aryl, 5-10 membered heteroaryl, and 3-10 membered heterocycyl, as defined herein. A non-limiting example includes free amino (i.e., —$NH_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

The term "acyloxy" refers to —OC(O)R where R is alkyl.

The term "alkoxy" or "alkyloxy" refers to OR where R is alkyl, or heteroalkyl, all optionally substituted.

The term "carboxyl" refers to a C(O)OH.

The term "oxo" refers to an =O group.

The term "halogen" or "halo" refers to F (fluoro), Cl (chloro), Br (bromo) and I (iodo).

The term "haloalkyl" refer to alkyl groups containing at least one halogen, in a further aspect are 1 to 3 haloatoms. Suitable haloatoms include F, Cl, and Br.

The term "haloacyl" refer to —C(O)-haloalkyl groups.

The term "alkenyl" refers to unsaturated groups which have 2 to 12 atoms and contain at least one carbon carbon double bond and includes straight chain, branched chain and cyclic groups. Alkenyl groups may be optionally substituted. Suitable alkenyl groups include allyl.

The term "alkynyl" refers to unsaturated groups which have 2 to 12 atoms and contain at least one carbon carbon triple bond and includes straight chain, branched chain and cyclic groups. Alkynyl groups may be optionally substituted. Suitable alkynyl groups include ethynyl.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Heteroaryl groups may be optionally substituted. Examples of heteroaryl groups include, but are not limited to, aromatic C3-8 heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In some embodiments, heteroaryl groups are optionally substituted with one or more substituents, independently selected from halo, hydroxy, amino, cyano, nitro, alkylamido, acyl, $C_{1-6}$-alkoxy, $C_{1-6}$-alkyl, $C_{1-6}$-hydroxyalkyl, C1-6-aminoalkyl, C1-6-alkylamino, alkylsulfenyl, alkylsulfinyl, alkylsulfonyl, sulfamoyl, or trifluoromethyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

As used herein, "cycloalkyl" means a fully saturated carbocyclyl ring or ring system. Examples include cyclopropyl, cyclobutyl, cyclopentyl, and cyclohexyl. The cycloalkyl group may have 3 to 10 carbon atoms (whenever it appears herein, a numerical range such as "3 to 10" refers to each integer in the given range. The cycloalkyl group may be designated as "$C_3$-$C_8$ cycloalkyl" or similar designations. By way of example only, "$C_3$-$C_8$ cycloalkyl" indicates that there are three to eight carbon atoms in the carbocyclyl ring or ring system.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O (oxygen), N (nitrogen) or S (sulfur), and in preferred five membered monocyclic heterocyclyls, the heteroatom(s) are selected from one or two heteroatoms selected from O (oxygen), N (nitrogen) or S (sulfur). Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH)CH$_2$—, and the like. Other radical naming conventions clearly indicate that the radical is a di-radical such as "alkylene" or "alkenylene."

When two R groups are said to form a ring (e.g., a carbocyclyl, heterocyclyl, aryl, or heteroaryl ring) "together with the atoms to which they are attached," it is meant that the collective unit of the atoms and the two R groups are the recited ring. The ring is not otherwise limited by the definition of each R group when taken individually. For example, when the following substructure is resent:

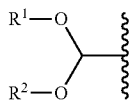

and R¹ and R² are defined as selected from the group consisting of alkyl and aryl, or R¹ and R² together with the oxygen to which they are each attached form a heterocyclyl, it is meant that R¹ and R² can be selected from alkyl or aryl, or alternatively, the substructure has structure:

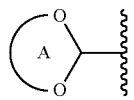

where ring A is a heterocyclic ring containing the depicted oxygens.

Similarly, when two "adjacent" R groups are said to form a ring "together with the atom to which they are attached," it is meant that the collective unit of the atoms, intervening bonds, and the two R groups are the recited ring. For example, when the following substructure is present:

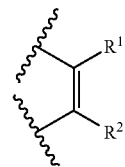

and R¹ and R² are defined as selected from the group consisting of hydrogen and alkyl, or R¹ and R² together with the atoms to which they are attached form an aryl or carbocyclyl, it is meant that R¹ and R² can be selected from hydrogen or alkyl, or alternatively, the substructure has structure:

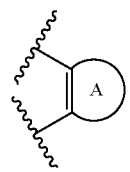

where A is an aryl ring or a carbocyclyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

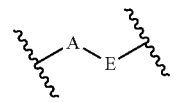

includes the substituent being oriented such that the A is attached at the leftnost attachment point of the molecule as well as the case in which A is attached at the rightmost attachment point of the molecule.

The phrase "therapeutically effective amount" means an amount of a compound or a combination of compounds that partially or fully ameliorates, attenuates or eliminates one or more of the symptoms of a particular disease or condition or prevents, modifies, or delays the onset of one or more of the symptoms of a particular disease or condition. Such amount can be administered as a single dosage or can be administered according to a regimen, whereby it is effective. Repeated administration may be needed to achieve a desired result (e.g., treatment of the disease and/or condition).

The term "pharmaceutically acceptable salt" includes salts of compounds of Formula I, II, III and IV derived from the combination of a compound of the present embodiments and an organic or inorganic acid or base. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, adipic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzenesulfonic acid, methanesulfonic acid, ethanesulfonic acid, p-toluenesulfonic acid, (+)-7,7-dimethyl-2-oxobicyclo[2.2.1]heptane-1-methanesulfonic acid, 1,2-ethanedisulfonic acid, dodecyl sulfonic acid, salicylic acid, glucoheptonic acid, gluconic acid, glucuronic acid, hippuric acid, hydrochloride hemiethanolic acid, 2-hydroxyethanesulfonic acid, lactic acid, lactobionic acid, methylbromide acid, methyl sulfuric acid, 2-naphthalenesulfonic acid, oleic acid, 4,4'-methylenebis-[3-hydroxy-2-naphthalenecarboxylic acid], polygalacturonic acid, stearic acid, sulfosalicylic acid, tannic acid, terephthalic acid and the like. Inorganic bases from which salts can be derived include, for example, bases that contain sodium, potassium, lithium, ammonium, calcium, magnesium, iron, zinc, copper, manganese, aluminum, and the like; particularly preferred are the ammonium, potassium, sodium, calcium and magnesium salts. In some embodiments, treatment of the compounds disclosed herein with an inorganic base results in loss of a labile hydrogen from the compound to afford the salt form including an inorganic cation such as $Li^+$, $Na^+$, $K^+$, $Mg^{2+}$ and $Ca^{2+}$ and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

Where the number of any given substituent is not specified (e.g., "haloalkyl"), there may be one or more substituents present. For example, "haloalkyl" can include one or more of the same or different halogens. For example, "haloalkyl" includes each of the substituents $CF_3$, $CHF_2$ and $CH_2F$.

The term "patient" refers to an animal being treated including a mammal, such as a dog, a cat, a cow, a horse, a sheep, and a human. In some embodiments, the patient is a mammal, either male or female. In some embodiments, the patient is a male or female human.

The term "prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g. HO—, HS—, HOOC—, $HOOPR_2$—, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are examples, not exhaustive, and one skilled in the art could prepare other known varieties of prodrugs. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, pharmacodynamic half-life, etc. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site specific delivery of the compound.

The term "stereoisomer" refers to the relative or absolute spatial relationship of the R group(s) attached to the stereogenic centers either carbon or phosphorus atoms, and refers to individual or any combination of the individual isomers such as a racemic mixture and a diastereomeric mixture. When a compound has two stereogenic centers, there are 4 potential stereoisomers.

The term "liver" refers to the liver organ.

The term "liver specificity" refers to the ratio:

[drug or a drug metabolite in liver tissue]/[drug or a drug metabolite in blood or another tissue]

as measured in animals treated with the drug or a prodrug. The ratio can be determined by measuring tissue levels at a specific time or may represent an AUC (area under a curve) based on values measured at three or more time points.

The term "increased or enhanced liver specificity" refers to an increase in liver specificity ratio in animals treated with the prodrug relative to animals treated with the parent drug.

The term "enhanced oral bioavailability" refers to an increase of at least about 50% of the absorption of the dose of the reference drug. In an additional aspect, the increase in oral bioavailability of the compound (compared to the reference drug) is at least about 100%, or a doubling of the absorption. Measurement of oral bioavailability usually refers to measurements of the prodrug, drug, or drug metabolite in blood, plasma, tissues, or urine following oral administration compared to measurements following parenteral administration.

The term "therapeutic index" refers to the ratio of the dose of a drug or prodrug that produces a therapeutically beneficial response relative to the dose that produces an undesired response such as death, an elevation of markers that are indicative of toxicity, and/or pharmacological side effects.

The term "sustained delivery" refers to an increase in the period in which there is a prolongation of therapeutically-effective drug levels due to the presence of the prodrug.

The terms "treating" or "treatment" of a disease includes inhibiting the disease (slowing or arresting or partially arresting its development), preventing the disease, providing relief from the symptoms or side effects of the disease (including palliative treatment), and/or relieving the disease (causing regression of the disease).

The terms "biological agent" refers to a compound that has biological activity or that has molecular properties that can be used for therapeutic or diagnosis purposes, such as a compound carrying a radioactive isotope or a heavy atom. In some embodiments, the biological agent may be a nucleoside or nucleoside analog portion of a monophosphate, diphosphate or triphosphate therapeutic agent. In some embodiments, the biological agent may be a nucleoside or nucleoside equivalent portion of a monophosphate therapeutic agent and corresponding diphosphate or triphosphate. In some embodiments, the biological agent may be a nucleoside equivalent portion of a monophosphonate therapeutic agent and corresponding monophosphate or diphosphate. Table 2 provides a list of the biological agents that can be enhanced with the phosphor(n)amidatacetal and phosph(on)atacetal compounds of Formula I.

TABLE 2

Known nucleoside and analogs with antiviral and anticancer activities

| Compound | Structure |
| --- | --- |
| Lamivudine | 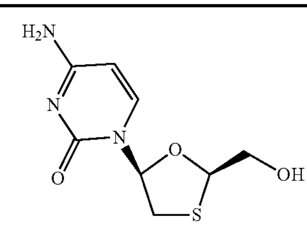 |
| Entecavir | 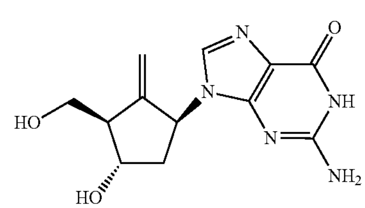 [SMILES: C=C1[C@H](CO)[C@@H](O)C[C@@H]1n1cnc2c(=O)[nH]c(N)nc21] |
| Telbivudine | 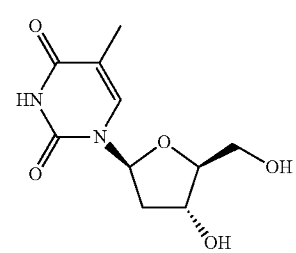 [SMILES: Cc1cn([C@@H]2C[C@@H](O)[C@H](CO)O2)c(=O)[nH]c1=O] |

TABLE 2-continued

Known nucleoside and analogs with antiviral and anticancer activities

| Compound | Structure |
|---|---|
| Cytarabine | 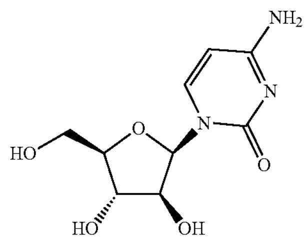 [SMILES: Nc1ccn([C@@H]2O[C@H](CO)[C@@H](O)[C@@H]2O)c(=O)n1] |
| MK-3682 nucleoside | 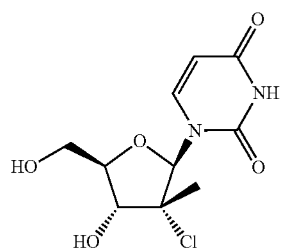 [SMILES: C[C@@]1(Cl)[C@H](O)[C@@H](CO)O[C@H]1n1ccc(=O)[nH]c1=O] |
| Vidarabine | 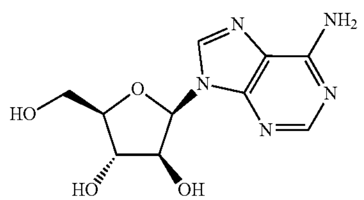 [SMILES: Nc1ncnc2c1ncn2[C@@H]1O[C@H](CO)[C@@H](O)[C@@H]1O] |
| PMEA | 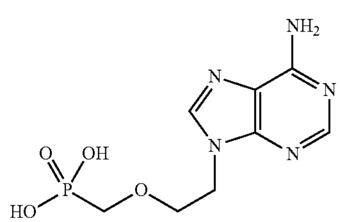 [SMILES: Nc1ncnc2c1ncn2CCOCP(=O)(O)O] |
| Cidofovir | 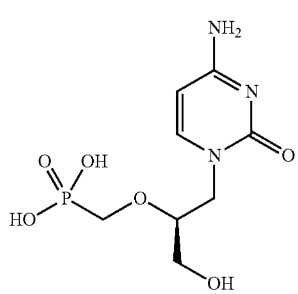 [SMILES: Nc1ccn(C[C@@H](CO)OCP(=O)(O)O)c(=O)n1] |
| Emitricitabine | 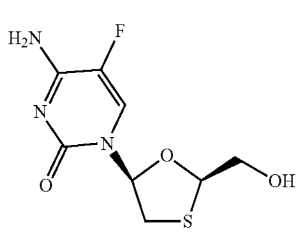 [SMILES: Nc1nc(=O)n([C@@H]2CS[C@H](CO)O2)cc1F] |
| Aciclovir | |
| Clevudine | |
| Ganciclovir | |
| 5-Fluorouridine | |

The terms "molecular pathway" refers to a series of molecular events in tissues such as a receptor modulating sequence, an enzyme modulating sequence, or a biosynthesis sequence that is involved in physiological or pathophysiological functions of a living animal.

Administration and Pharmaceutical Compositions

The disclosed compounds may be used alone or in combination with other treatments. These compounds, when used in combination with other agents, may be administered as a daily dose or an appropriate fraction of the daily dose (e.g., bid). The compounds may be administered after a course of treatment by another agent, during a course of therapy with another agent, administered as part of a therapeutic regimen, or may be administered prior to therapy with another agent in a treatment program.

Examples of pharmaceutically acceptable salts include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, palmoate, phosphate, polygalacturonate, stearate, succinate, sulfate, sulfosalicylate, tannate, tartrate, terphthalate, tosylate, and triethiodide.

Compositions containing the active ingredient may be in any form suitable for the intended method of administration. In some embodiments, the compounds of a method and/or composition described herein can be provided via oral administration, rectal administration, transmucosal administration, intestinal administration, enteral administration, topical administration, transdermal administration, intrathecal administration, intraventricular administration, intraperitoneal administration, intranasal administration, intraocular administration and/or parenteral administration.

When the compounds are administered via oral administration, for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient can be mixed with an inert solid diluent, for example calcium phosphate or kaolin, or as soft gelatin capsules wherein the active ingredient can be mixed with water or an oil medium, such as peanut oil, liquid paraffin or olive oil.

Formulations suitable for parenteral administration include aqueous and non-aqueous isotonic sterile injection solutions which may contain, for example, antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

In some embodiments unit dosage formulations contain a daily dose or unit, daily sub-dose, or an appropriate fraction thereof, of a drug. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

The actual dose of the compounds described herein depends on the specific compound, and on the condition to be treated; the selection of the appropriate dose is well within the knowledge of the skilled artisan. In some embodiments, a daily dose may be from about 0.1 mg/kg to about 100 mg/kg or more of body weight, from about 0.25 mg/kg or less to about 50 mg/kg, from about 0.5 mg/kg or less to about 25 mg/kg, from about 1.0 mg/kg to about 10 mg/kg of body weight. Thus, for administration to a 70 kg person, the dosage range would be from about 7 mg per day to about 7000 mg per day, from about 35 mg per day or less to about 2000 mg per day or more, from about 70 mg per day to about 1000 mg per day.

Methods of Treatment

Some embodiments of the present invention include methods of treating a disease, disorder or condition is selected from the group consisting of hepatitis, liver cancer, liver fibrosis, fatty liver, malaria, viral infection, parasitic infection, diabetes, hyperlipidemia, atherosclerosis, obesity, dyslipidemia, hyperglycemia, a hormonal condition, HIV, and various types of cancer with the compounds, and compositions comprising compounds described herein. Some methods include administering a compound, composition, pharmaceutical composition described herein to a subject in need thereof. In some embodiments, a subject can be an animal, e.g., a mammal, a human. In some embodiments, the subject is a human.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament or additional therapeutic agent(s). By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment, the agents are administered through the same route, such as orally. In another embodiment, the agents are administered through different routes, such as one being administered orally and another being administered i.v.

Examples of additional medicaments include a therapeutic agent(s) selected from the group consisting of thymosin alpha-1, interferon-λ, an inhibitor of HCV protease, an inhibitor of HCV NS5A replication complex, an inhibitor of HCV NS5B polymerase, an inhibitor of HCV helicase, a cyclophilin inhibitor, an inhibitor of inosine monophosphate dehydrogenase, ribavirin, interferon-α, and pegylated interferon-α. In some embodiments, additional medicaments include one or more of cobicistat, emtricitabine and elvitegravir. In some embodiments, additional medicaments include two or more of cobicistat, emtricitabine and elvitegravir. In some embodiments, additional medicaments include cobicistat, emtricitabine and elvitegravir. In some embodiments, additional medicaments include one or more of ribavirin, peginterferon-alfa, simeprevir, ledipasvir and daclatasvir. In some embodiments, the additional therapeutic agent may be one or more of cobicistat, emtricitabine and elvitegravir. In some embodiments, the additional therapeutic agent may be two or more of cobicistat, emtricitabine and elvitegravir. In some embodiments, the additional therapeutic agent may be cobicistat, emtricitabine and elvitegravir. In some embodiments, the additional therapeutic agent may be one or more of ribavirin, peginterferon-alfa, simeprevir, ledipasvir and daclatasvir. In some embodiments, the additional therapeutic agent for HBV treatment may be one or more of a HBV entry inhibitor, a HBV cccDNA inhibitor, a HBV capsid inhibitor, an interferon, HBV assembly inhibitor. In some embodiments, the additional therapeutic agent for HCC treatment may be one or more of sorafenib, regorafenib, an immune-oncology agent such as a PD-1 or PD-L1 checkpoint inhibitor.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

Synthesis of Compounds

The following procedures for the preparation of the new compounds illustrate the general procedures used to prepare the phosphor(n)amidatacetal and phosph(on)atacetal drugs. A protecting group can be introduced at different stages of synthesis of a drug. In some embodiments, they are introduced at a later stage, because of the general sensitivity of these groups to various reaction conditions. Optically pure compounds containing a single isomer at the phosphorus center can be made, for example, by separation of the diastereomers by a combination of column chromatography and/or crystallization, or by enantioselective synthesis of chiral activated phosph(on)ate intermediates.

Scheme I describes general strategies of synthesis of the compounds of Formula I. The compound of structure 1 is condensed with an optionally substituted phenol or naphthol of structure 2 in the presence of a base to give a product of structure 3. Acetal compound of structure 4 is prepared from the corresponding aldehyde by the standard procedure in the literature. Reaction of the compounds of structures 3 and 4 in the presence of a base affords the final product of structure 5. Alternatively, the aryloxy phosphate chloride of structure 6 is couple with acetal compound of structure 4 to provide intermediate of structure 7 that reacts with the active-containing compound of structure 8 to yield the final product of structure 5.

Scheme I

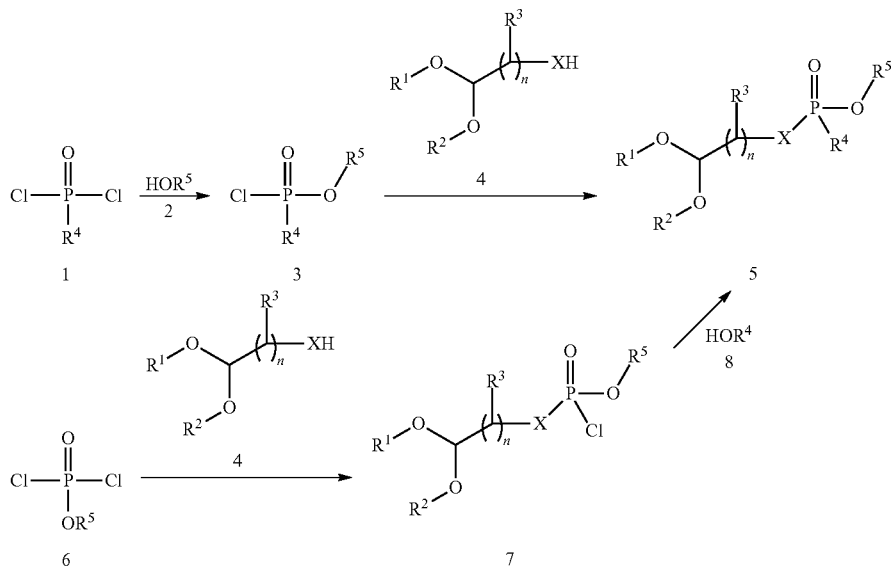

EXAMPLES

Some compounds of Formula I, II, III, IV, V, and VI are prepared as outlined below.

Example 1

(2R,3R,4R,5R)-2-((((((S)-1-(1,3-Dioxolan-2-yl)ethyl)amino)(phenoxy)phosphoryl)oxy)methyl)-5-(2,4-dioxo-3,4-dihydropyrimidin-1(2H)-yl)-4-fluoro-4-methyltetrahydrofuran-3-yl propionate (Compound 101)

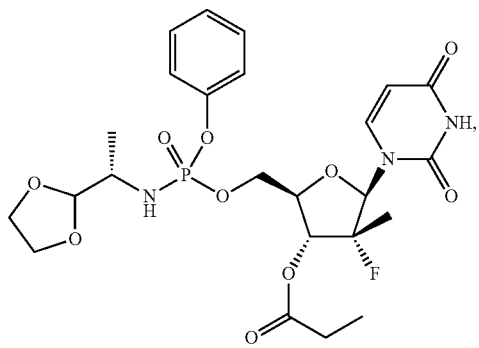 [SMILES: CCC(=O)O[C@@H]1[C@@H](COP(=O)(N[C@@H](C)C2OCCO2)Oc2ccccc2)O[C@@H](n2ccc(=O)[nH]c2=O)[C@]1(C)F]

Compound 101 was prepared according to Scheme I from phenyl phosphorodichloridate, (S)—N-Cbz-2-aminopropanol, and 2'-deoxy-2'-fluoro-2'-C-methyl-3'-propionyloxyuridine as follows.

(S)—N-Cbz-2-aminopropanal (S)—N-Cbz-2-aminopropanol (10 g, 48 mmol) was refluxed with 2-iodoxybenzoic acid (IBX) (34 g, 120 mmol) in EtOAc (300 mL) for 2-4 hours. After completion of the reaction (monitored by TLC), the IBX was filtered through celite. The filtrate was concentrated to dryness under vacuum to give the product (9.5 g, 94%).

(S)-1-(1,3-Dioxolan-2-yl)-ethan-1-amine:

A suspension mixture of the above aldehyde (5.0 g, 24 mmol), ethylene glycol (7.6 g, 122 mmol), PPTS (0.6 g, 2.4 mmol), and triethyl orthoformate (3.6 g, 24 mmol) in toluene (50 mL) was stirred at 80° C. for 12 hours. The reaction mixture was washed sequentially with aqueous HCl (IM), NaHCO$_3$(saturated), and brine, dried over Na$_2$SO$_4$, and concentrated. Silica gel chromatography (PE:EA=4:1) of the crude gave the N-Cbz protected product in 50% yield (3.0 g). A suspension mixture of the N-Cbz-amine (2 g) and activated Pd/C (20% by weight) in ethyl acetate (30 mL) was stirred overnight at room temperature in the presence of hydrogen gas (H$_2$ balloon). The Pd/C was filtered through celite and the filtrate was concentrated to dryness under vacuum to give the product.

Phenyl ((S)-1-(1,3-dioxolan-2-yl)-3-methylbutyl) phosphoramidochloridate

To a solution of phenyl phosphorodichloridate (0.4 g, 1.9 mmol) in dichloromethane at −78° C. was added the above compound (0.2 g, 1.7 mmol) in the presence of excess triethylamine and the resulting mixture was stirred for 2 hours. Standard work-up procedure afforded the crude product in ~60% yield (0.3 g).

Compound 101:

To a solution of the crude phenyl phosphoramidochloridate in dichloromethane (0.5 mL) was added a solution of 2'-deoxy-2'-fluoro-2'-C-methyl-3'-propionyloxyuridine (0.2 g, 1.2 mmol) and N-methylimidazole (0.4 g, 5 mmol) in dichloromethane (0.5 mL) at −78° C. under nitrogen. The reaction mixture was slowly allowed to warm to room temperature and stirred for one hour. Standard work-up followed by Pre-HPLC to give compound 101 as a mixture (3:2) of two diastereomers (120 mg, 44%).

[M+H]$^+$ calculated for C$_{24}$H$_{31}$FN$_3$O$_{10}$P: 572.18; found: 572.05. $^1$H NMR (300 MHz, CD$_3$OD) 7.68 (d, J=8.1, 1H) (major), 7.62 (d, J=8.1, 1H) (minor), 7.40-7.10 (m, 5H), 5.68 (d, J=8.1, 1H) (major), 5.49 (d, J=8.1, 1H) (minor), 1.34 (d, J=22.5, 3H) (major), 1.33 (d, J=22.5, 3H) (minor).

Example 2

((2R,3R,4R,5R)-5-(2,4-Dioxo-3,4-dihydropyrimidin-1(2H)-yl)-4-fluoro-3-hydroxy-4-methyltetrahydrofuran-2-yl)methyl phenyl (S)—((S)-1-(1,3-dioxolan-2-yl)-3-methylbutyl)phosphoramidate (Compound 102)

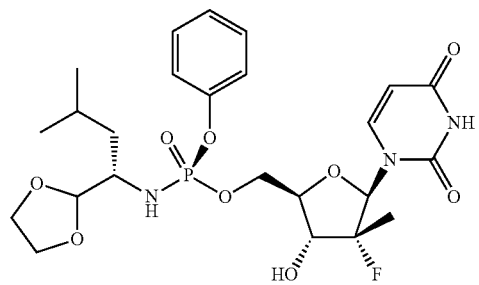 [SMILES: CC(C)C[C@H](N[P@](=O)(OC[C@H]1O[C@@H](n2ccc(=O)[nH]c2=O)[C@](C)(F)[C@@H]1O)Oc1ccccc1)C1OCCO1]

Compound 102 was prepared according to Scheme I in a similar fashion as described in Example 1 from phenyl phosphorodichloridate, (S)—N-Cbz-2-amino-4-methylpentanol, and 2'-deoxy-2'-fluoro-2'-C-methyluridine. [M+H]$^+$ calculated for C$_{24}$H$_{33}$FN$_3$O$_9$P: 558.20; found: 558.35.

Example 3

((2R,3R,4R,5R)-5-(2,4-Dioxo-3,4-dihydropyrimidin-1(2H)-yl)-4-fluoro-3-hydroxy-4-methyltetrahydrofuran-2-yl)methyl phenyl (R)—((S)-1-(1,3-dioxolan-2-yl)-3-methylbutyl)phosphoramidate (Compound 103)

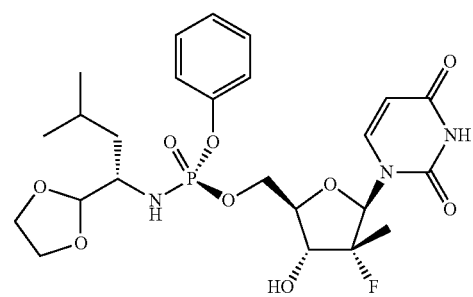 [SMILES: CC(C)C[C@H](N[P@@](=O)(OC[C@H]1O[C@@H](n2ccc(=O)[nH]c2=O)[C@](C)(F)[C@@H]1O)Oc1ccccc1)C1OCCO1]

Compound 103 was isolated as a minor diastereomer from Example 2. [M+H]$^+$ calculated for C$_{24}$H$_{33}$FN$_3$O$_9$P: 558.20; found: 558.30.

Example 4

2,3-Dimethylphenyl (((2R,3R,4R,5R)-5-(2,4-dioxo-3,4-dihydropyrimidin-1(2H)-yl)-4-fluoro-3-hydroxy-4-methyltetrahydrofuran-2-yl)methyl) ((S)-1-(1,3-dioxepan-2-yl)ethyl)phosphoramidate (Compound 104

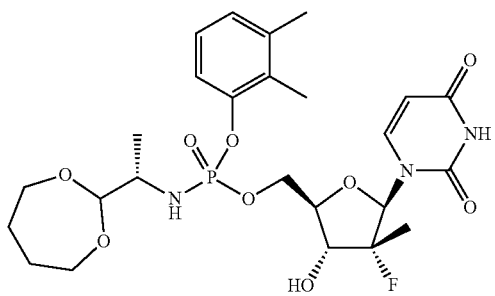 [SMILES: Cc1cccc(OP(=O)(N[C@@H](C)C2OCCCCO2)OC[C@H]2O[C@@H](n3ccc(=O)[nH]c3=O)[C@](C)(F)[C@@H]2O)c1C]

Compound 104 was prepared as a mixture of two diastereomers according to Scheme I in a similar fashion as described in Example 1 from 2,3-dimethylphenyl phosphorodichloridate, (S)—N-Cbz-2-aminopropanol, and 2'-deoxy-2'-fluoro-2'-C-methyluridine. [M+H]$^+$ calculated for $C_2H_{35}FN_3O_9P$: 572.22; found: 572.2.

Example 5

(2R,3R,4R,5R)-2-((((((S)-1-(1,3-Dioxolan-2-yl)ethyl)amino)phenoxy)phosphoryl)oxy)methyl)-5-(2,4-dioxo-3,4-dihydropyrimidin-1(2H)-yl)-4-fluoro-4-methyltetrahydrofuran-3-yl butyrate (Compound 105)

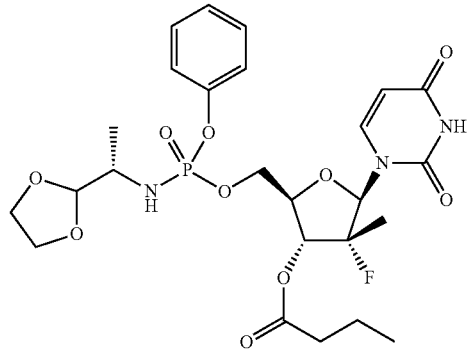 [SMILES: CCCC(=O)O[C@@H]1[C@@H](COP(=O)(N[C@@H](C)C2OCCO2)Oc2ccccc2)O[C@@H](n2ccc(=O)[nH]c2=O)[C@]1(C)F]

Compound 105 was prepared as a mixture of two diastereomers according to Scheme I in a similar fashion as described in Example 1 from phenyl phosphorodichloridate, (S)—N-Cbz-2-aminopropanol, and 2'-deoxy-2'-fluoro-2'-C-methyl-3'-butyryloxyuridine. [M+H]$^+$ calculated for $C_{25}H_{33}FN_3O_{10}P$: 586.20; found: 586.20.

Example 6

(2R,3R,4R,5R)-2-((((((S)-1-(1,3-Dioxolan-2-yl)ethyl)amino)phenoxy)phosphoryl)oxy)methyl)-5-(2,4-dioxo-3,4-dihydropyrimidin-1(2H)-yl)-4-fluoro-4-methyltetrahydrofuran-3-yl pentanoate (Compound 106)

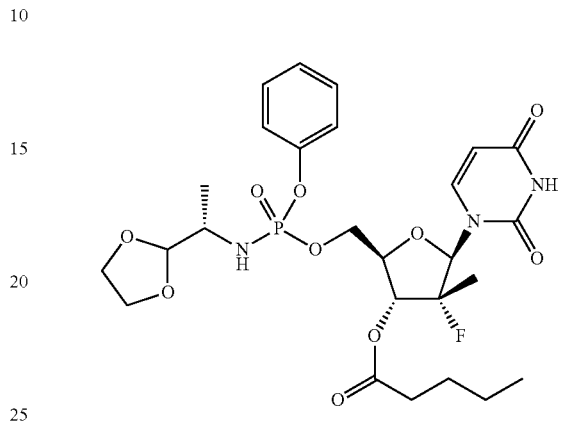

Compound 106 was prepared as a mixture of two diastereomers according to Scheme I in a similar fashion as described in Example 1 from phenyl phosphorodichloridate, (S)—N-Cbz-2-aminopropanol, and 2'-deoxy-2'-fluoro-2'-C-methyl-3'-pentanoinyloxyuridine. [M+H]$^+$ calculated for $C_{26}H_{35}FN_3O_{10}P$: 600.21; found: 600.25.

Example 7

(2R,3R,4R,5R)-2-((((((S)-1-(1,3-Dioxolan-2-yl)ethyl)amino)(naphthalen-1-yloxy)phosphoryl)oxy)methyl)-5-(2,4-dioxo-3,4-dihydropyrimidin-1(2H)-yl)-4-fluoro-4-methyltetrahydrofuran-3-yl propionate (Compound 107)

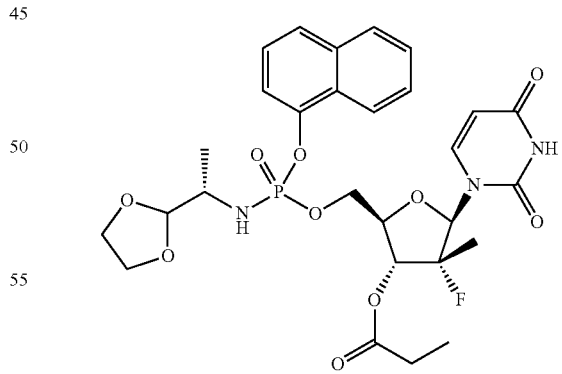

Compound 107 was prepared as a mixture of two diastereomers according to Scheme I in a similar fashion as described in Example 1 from 1-naphthyl phosphorodichloridate, (S)—N-Cbz-2-aminopropanol, and 2'-deoxy-2'-fluoro-2'-C-methyl-3'-propionyloxyuridine. [M+H]$^+$ calculated for $C_{28}H_{33}FN_3O_{10}P$: 622.20; found: 622.25.

Example 8

(2R,3R,4R,5R)-2-((((((S)-1-(1,3-Dioxan-2-yl)ethyl)amino)phenoxy)phosphoryl)oxy)methyl)-5-(2,4-dioxo-3,4-dihydropyrimidin-1(2H)-yl)-4-fluoro-4-methyltetrahydrofuran-3-yl propionate (Compound 108)

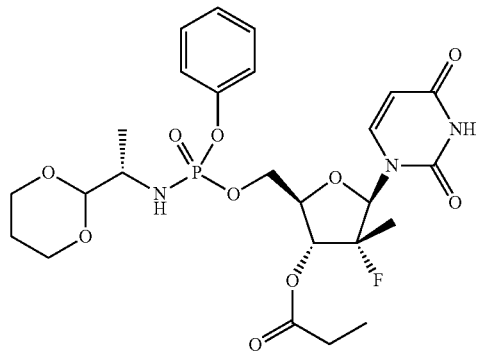 [SMILES: CCC(=O)O[C@@H]1[C@@H](COP(=O)(N[C@@H](C)C2OCCCO2)Oc2ccccc2)O[C@@H](n2ccc(=O)[nH]c2=O)[C@]1(C)F]

Compound 108 was prepared as a mixture of two diastereomers according to Scheme I in a similar fashion as described in Example 1 from phenyl phosphorodichloridate, (S)—N-Cbz-2-aminopropanol, and 2'-deoxy-2'-fluoro-2'-C-methyl-3'-propionyloxyuridine. [M+H]$^+$ calculated for $C_{25}H_{33}FN_3O_{10}P$: 586.20; found: 586.20.

Example 9

(2R,3R,4R,5R)-2-((((((S)-1-(1,3-Dioxolan-2-yl)ethyl)amino)(phenoxy)phosphoryl)oxy)methyl)-5-(2,4-dioxo-3,4-dihydropyrimidin-1(2H)-yl)-4-fluoro-4-methyltetrahydrofuran-3-yl hexanoate (Compound 109)

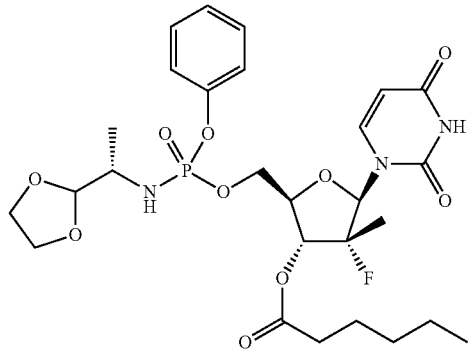 [SMILES: CCCCCC(=O)O[C@@H]1[C@@H](COP(=O)(N[C@@H](C)C2OCCO2)Oc2ccccc2)O[C@@H](n2ccc(=O)[nH]c2=O)[C@]1(C)F]

Compound 109 was prepared as a mixture of two diastereomers according to Scheme I in a similar fashion as described in Example 1 from phenyl phosphorodichloridate, (S)—N-Cbz-2-aminopropanol, and 2'-deoxy-2'-fluoro-2'-C-methyl-3'-hexanoyloxyuridine. [M+H]$^+$ calculated for $C_{27}H_{37}FN_3O_{10}P$: 614.23; found: 614.25.

Example 10

(2R,3R,4R,5R)-5-(2,4-Dioxo-3,4-dihydropyrimidin-1(2H)-yl)-2-((((((1S)-1-(4-ethyl-1,3-dioxolan-2-yl)ethyl)amino)(phenoxy)phosphoryl)oxy)methyl)-4-fluoro-4-methyltetrahydrofuran-3-yl propionate (Compound 110)

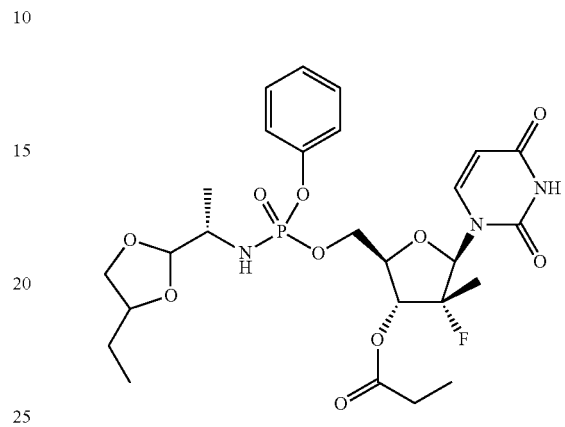

Compound 110 was prepared as a mixture of four diastereomers according to Scheme I in a similar fashion as described in Example 1 from phenyl phosphorodichloridate, (S)—N-Cbz-2-aminopropanol, and 2'-deoxy-2'-fluoro-2'-C-methyl-3'-propionyloxyuridine. [M+H]$^+$ calculated for $C_{26}H_{35}FN_3O_{10}P$: 600.20; found: 600.30.

Example 11

(2R,3R,4R,5R)-2-((((((S)-1-(1,3-Dioxepan-2-yl)ethyl)amino)(phenoxy)phosphoryl)oxy)methyl)-5-(2,4-dioxo-3,4-dihydropyrimidin-1(2H)-yl)-4-fluoro-4-methyltetrahydrofuran-3-yl propionate (Compound 111)

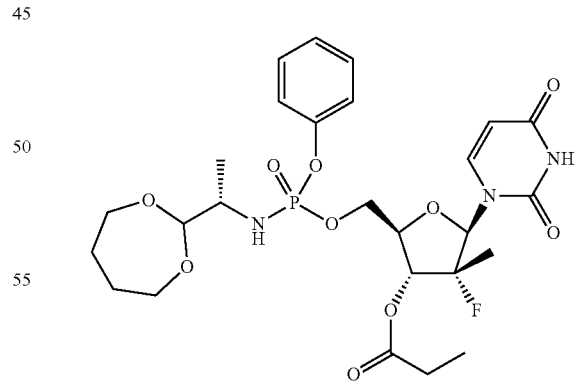

Compound 111 was prepared as a mixture of four diastereomers according to Scheme I in a similar fashion as described in Example 1 from phenyl phosphorodichloridate, (S)—N-Cbz-2-aminopropanol, and 2'-deoxy-2'-fluoro-2'-C-methyl-3'-propionyloxyuridine. [M+H]$^+$ calculated for $C_{26}H_{35}FN_3O_{10}P$: 600.20; found: 600.25.

Example 12

(2R,3R,4R,5R)-2-((((((S)-1-(1,3-Dioxolan-2-yl)propyl)amino)(phenoxy)phosphoryl)oxy)methyl)-5-(2,4-dioxo-3,4-dihydropyrimidin-1(2H)-yl)-4-fluoro-4-methyltetrahydrofuran-3-yl propionate (Compound 112)

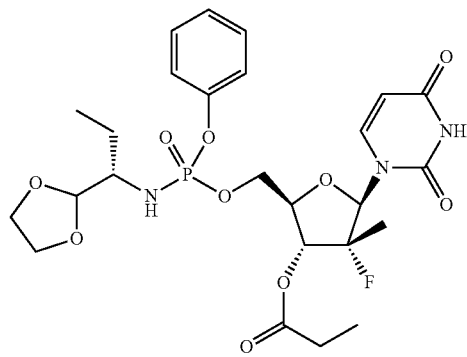 [SMILES: CCC(=O)O[C@@H]1[C@@H](COP(=O)(N[C@@H](CC)C2OCCO2)Oc2ccccc2)O[C@@H](n2ccc(=O)[nH]c2=O)[C@]1(C)F]

Compound 112 was prepared as a mixture of two diastereomers according to Scheme I in a similar fashion as described in Example 1 from phenyl phosphorodichloridate, (S)—N-Cbz-2-aminobutanol, and 2'-deoxy-2'-fluoro-2'-C-methyl-3'-propionyloxyuridine. [M+H]$^+$ calculated for $C_{25}H_{33}FN_3O_{10}P$: 586.20; found: 586.25.

Example 13

(2R,3R,4R,5R)-2-((((((1S)-1-(4,5-Dimethyl-1,3-dioxolan-2-yl)ethyl)amino)(phenoxy)phosphoryl)oxy)methyl)-5-(2,4-dioxo-3,4-dihydropyrimidin-1(2H)-yl)-4-fluoro-4-methyltetrahydrofuran-3-yl propionate (Compound 113)

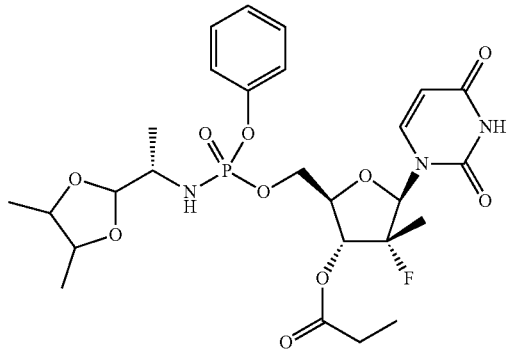 [SMILES: CCC(=O)O[C@@H]1[C@@H](COP(=O)(N[C@@H](C)C2OC(C)C(C)O2)Oc2ccccc2)O[C@@H](n2ccc(=O)[nH]c2=O)[C@]1(C)F]

Compound 113 was prepared as a mixture of four diastereomers according to Scheme I in a similar fashion as described in Example 1 from phenyl phosphorodichloridate, (S)—N-Cbz-2-aminopropanol, and 2'-deoxy-2'-fluoro-2'-C-methyl-3'-propionyloxyuridine. [M+H]$^+$ calculated for $C_{26}H_{35}FN_3O_{10}P$: 600.20; found: 600.25.

Example 14

(2R,3R,4R,5R)-2-(((((S)-1-(1,3-Dioxolan-2-yl)propoxy)(phenoxy)phosphoryl)oxy)methyl)-5-(2,4-dioxo-3,4-dihydropyrimidin-1(2H)-yl)-4-fluoro-4-methyltetrahydrofuran-3-yl propionate (Compound 114A) and (2R,3R,4R,5R)-2-(((((R)-1-(1,3-dioxolan-2-yl)propoxy)(phenoxy)phosphoryl)oxy)methyl)-5-(2,4-dioxo-3,4-dihydropyrimidin-1(2H)-yl)-4-fluoro-4-methyltetrahydrofuran-3-ylpropionate (Compound 114B)

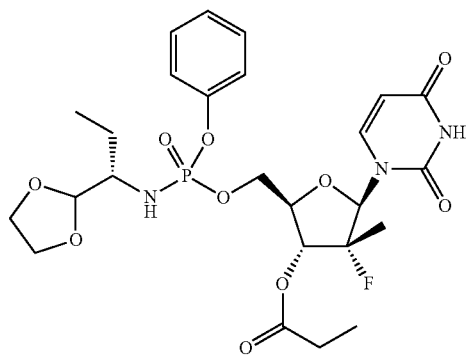

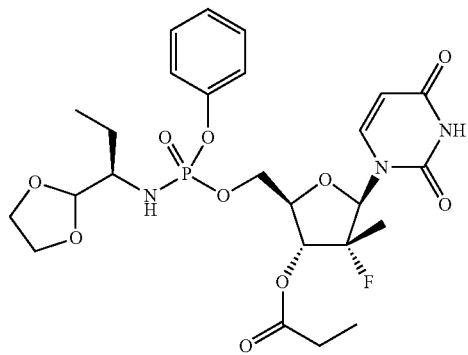

Compounds 114A and 114B were prepared and separated by HPLC as two individual mixtures of two diastereomers according to Scheme I in a similar fashion as described in Example 1 from phenyl phosphorodichloridate, 2-hydroxybutanal, and 2'-deoxy-2'-fluoro-2'-C-methyl-3'-propionyloxyuridine. [M+H]$^+$ calculated for $C_{25}H_{32}FN_2O_{10}P$: 587.18; found: 587.2.

Example 15

2,3-Dimethylphenyl (((2R,3R,4R,5R)-5-(2,4-dioxo-3,4-dihydropyrimidin-1(2H)-yl)-4-fluoro-3-hydroxy-4-methyltetrahydrofuran-2-yl)methyl) ((S)-1-(1,3-dioxepan-2-yl)ethyl)phosphoramidate (Compound 115)

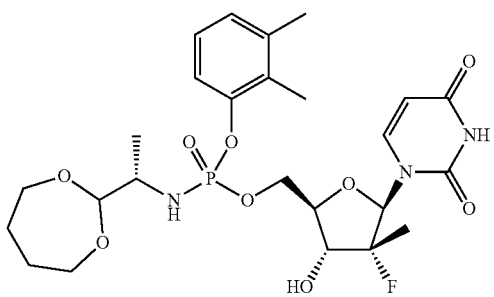 [SMILES: Cc1cccc(OP(=O)(N[C@@H](C)C2OCCCCO2)OC[C@H]2O[C@@H](n3ccc(=O)[nH]c3=O)[C@](C)(F)[C@@H]2O)c1C]

Compound 115 was prepared as a mixture of two diastereomers according to Scheme I in a similar fashion as described in Example 1 from 2,3-dimethylphenyl phosphorodichloridate, (S)—N-Cbz-2-aminopropanol, and 2'-deoxy-2'-fluoro-2'-C-methyl-3'-propionyloxyuridine. [M+H]$^+$ calculated for $C_{25}H_{35}FN_3O_9P$: 572.22; found: 572.2.

Example 16

Phenyl N—((S)-1-(1,3-dioxolan-2-yl)ethyl)-P—((((R)-1-(6-amino-9H-purin-9-yl)propan-2-yl)oxy)methyl)phosphonamidate (Compound 116)

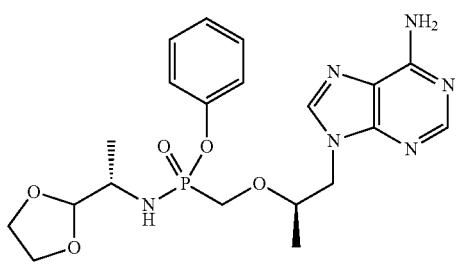 [SMILES: C[C@H](Cn1cnc2c(N)ncnc21)OCP(=O)(N[C@@H](C)C1OCCO1)Oc1ccccc1]

Compound 11 was prepared as a mixture of two diastereomers according to Scheme I from phenol, (S)—N-Cbz-2-aminopropanol, and (R)-(((1-(6-amino-9H-purin-9-yl)propan-2-yl)oxy)methyl)phosphonic dichloride. [M+H]$^+$ calculated for $C_{20}H_{27}N_6O_5P$: 463.19; found: 463.1.

Example 17

Phenyl N—((S)-1-(1,3-dioxolan-2-yl)-3-methylbutyl)-P—((((R)-1-(6-amino-9H-purin-9-yl)propan-2-yl)oxy)methyl)phosphonamidate (Compound 117)

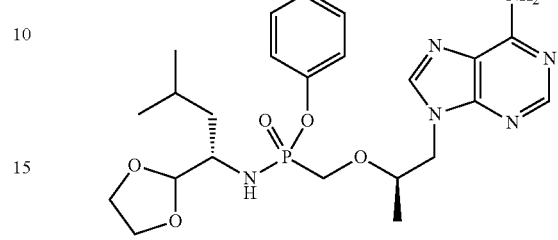

Compound 117 was prepared as a mixture of two diastereomers according to Scheme I from phenol, (S)—N-Cbz-2-amino-4-methylpentanol, and (R)-(((1-(6-amino-9H-purin-9-yl)propan-2-yl)oxy)methyl)phosphonic dichloride. [M+H]$^+$ calculated for $C_{23}H_{33}N_6O_5P$: 505.24; found: 505.2.

Example 18

Phenyl P—((((R)-1-(6-amino-9H-purin-9-yl)propan-2-yl)oxy)methyl)-N-(1-(4-ethyl-1,3-dioxolan-2-yl)propan-2-yl)phosphonamidate (Compound 118)

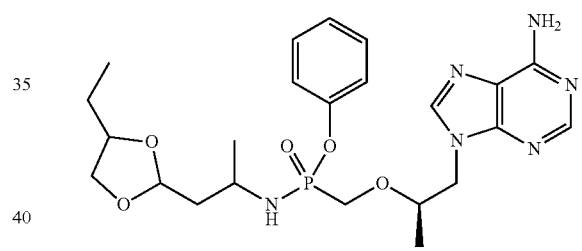

Compound 118 was prepared as a mixture of four or more diastereomers according to Scheme I from phenol, (S)—N-Cbz-3-aminobutanol, and (R)-(((1-(6-amino-9H-purin-9-yl)propan-2-yl)oxy)methyl)phosphonic dichloride. [M+H]$^+$ calculated for $C_{23}H_{33}N_6O_5P$: 505.24; found: 505.2.

Example 19

Phenyl N—((S)-1-(1,3-dioxolan-2-yl)propyl)-P—((((R)-1-(6-amino-9H-purin-9-yl)propan-2-yl)oxy)methyl)phosphonamidate (Compound 119)

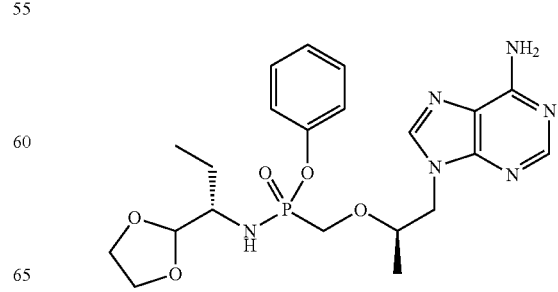

Compound 119 was prepared as a mixture of two diastereomers according to Scheme I from phenol, (S)—N-Cbz-2-aminobutanol, and (R)-(((1-(6-amino-9H-purin-9-yl)propan-2-yl)oxy)methyl)phosphonic dichloride. [M+H]$^+$ calculated for $C_{21}H_{29}N_6O_5P$: 477.20; found: 477.2.

Example 20

Phenyl N—((S)-1-(1,3-dioxan-2-yl)ethyl)-P—((((R)-1-(6-amino-9H-purin-9-yl)propan-2-yl)oxy)methyl)phosphonamidate (Compound 120)

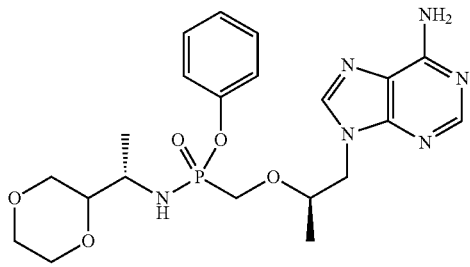 [SMILES: C[C@H](Cn1cnc2c(N)ncnc21)OCP(=O)(N[C@@H](C)C1COCCO1)Oc1ccccc1]

Compound 120 was prepared as a mixture of two diastereomers according to Scheme I from phenol, (S)—N-Cbz-2-aminopropanol, and (R)-(((1-(6-amino-9H-purin-9-yl)propan-2-yl)oxy)methyl)phosphonic dichloride. [M+H]$^+$ calculated for $C_{21}H_{29}N_6O_5P$: 477.20; found: 477.2.

Example 21

3,5-Dimethylphenyl N—((S)-1-(1,3-dioxolan-2-yl)ethyl)-P—((((R)-1-(6-amino-9H-purin-9-yl)propan-2-yl)oxy)methyl)phosphonamidate (Compound 121)

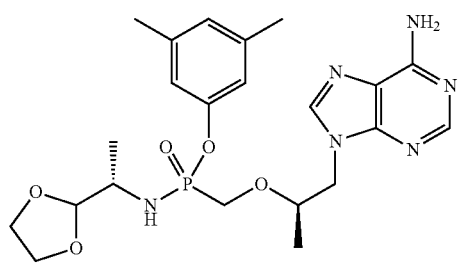 [SMILES: Cc1cc(C)cc(OP(=O)(CO[C@H](C)Cn2cnc3c(N)ncnc32)N[C@@H](C)C2OCCO2)c1]

Compound 121 was prepared as a mixture of two diastereomers according to Scheme I from 3,5-dimethylphenol, (S)—N-Cbz-2-aminopropanol, and (R)-(((1-(6-amino-9H-purin-9-yl)propan-2-yl)oxy)methyl)phosphonic dichloride. [M+H]$^+$ calculated for $C_{22}H_{31}N_6O_5P$: 491.22; found: 491.2.

Example 22

Phenyl N—((S)-1-(1,3-dioxepan-2-yl)ethyl)-P—((((R)-1-(6-amino-9H-purin-9-yl)propan-2-yl)oxy)methyl)phosphonamidate (Compound 122)

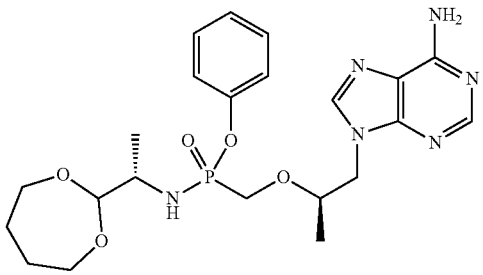 [SMILES: C[C@H](Cn1cnc2c(N)ncnc21)OCP(=O)(N[C@@H](C)C1OCCCCO1)Oc1ccccc1]

Compound 122 was prepared as a mixture of two diastereomers according to Scheme I from phenol, (S)—N-Cbz-2-aminopropanol, and (R)-(((1-(6-amino-9H-purin-9-yl)propan-2-yl)oxy)methyl)phosphonic dichloride. [M+H]$^+$ calculated for $C_{22}H_{31}N_6O_5P$: 491.22; found: 491.2.

Example 23

Phenyl N—((S)-1-(1,3-dioxolan-2-yl)-2-methylpropyl)-P—((((R)-1-(6-amino-9H-purin-9-yl)propan-2-yl)oxy)methyl)phosphonamidate (Compound 123)

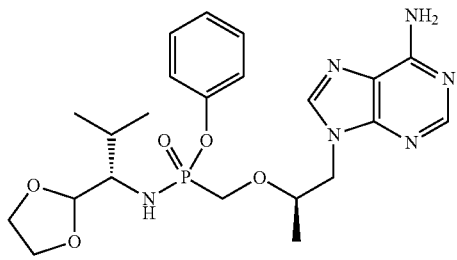 [SMILES: CC(C)[C@H](NP(=O)(CO[C@H](C)Cn1cnc2c(N)ncnc21)Oc1ccccc1)C1OCCO1]

Compound 123 was prepared as a mixture of two diastereomers according to Scheme I from phenol, (S)—N-Cbz-2-amino-3-methylbutanol, and (R)-(((1-(6-amino-9H-purin-9-yl)propan-2-yl)oxy)methyl)phosphonic dichloride. [M+H]$^+$ calculated for $C_{22}H_{31}N_6OP$: 491.22; found: 491.2.

Example 24

Phenyl N—((S)-1-(1,3-dioxolan-2-yl)-2-phenyl-ethyl)-P—((((R)-1-(6-amino-9H-purin-9-yl)propan-2-yl)oxy)methyl)phosphonamidate (Compound 124)

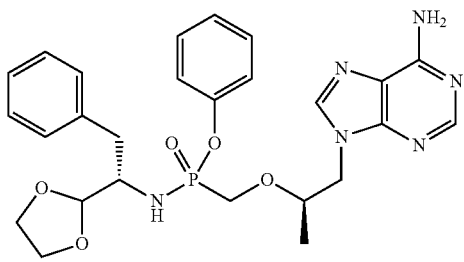 [SMILES: C[C@H](Cn1cnc2c(N)ncnc21)OCP(=O)(N[C@@H](Cc1ccccc1)C1OCCO1)Oc1ccccc1]

Compound 124 was prepared as a mixture of two diastereomers according to Scheme I from phenol, (S)—N-Cbz-2-amino-3-phenylpropanol, and (R)-(((1-(6-amino-9H-purin-9-yl)propan-2-yl)oxy)methyl)phosphonic dichloride. [M+H]$^+$ calculated for $C_{26}H_{35}N_6O_5P$: 539.22; found: 539.2.

Example 25

Phenyl N—((S)-1-(1,3-dioxocan-2-yl)ethyl)-P—((((R)-1-(6-amino-9H-purin-9-yl)propan-2-yl)oxy)methyl)phosphonamidate (Compound 125)

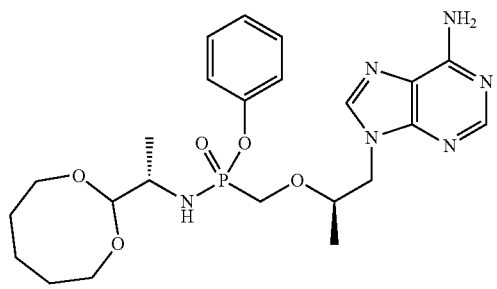 [SMILES: C[C@H](Cn1cnc2c(N)ncnc21)OCP(=O)(N[C@@H](C)C1OCCCCCO1)Oc1ccccc1]

Compound 125 can be prepared as a mixture of two diastereomers according to Scheme I from phenol, (S)—N-Cbz-2-aminopropanol, and (R)-(((1-(6-amino-9H-purin-9-yl)propan-2-yl)oxy)methyl)phosphonic dichloride.

Example 26

2,3-Dimethylphenyl N—((S)-1-(1,3-dioxepan-2-yl)ethyl)-P—((((R)-1-(6-amino-9H-purin-9-yl)propan-2-yl)oxy)methyl)phosphonamidate (Compound 126)

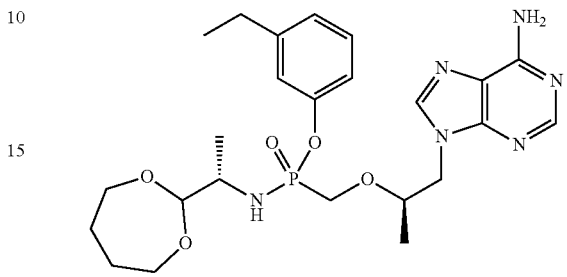

Compound 126 was prepared as a mixture of two diastereomers according to Scheme I from 3-ethylphenol, (S)—N-Cbz-2-aminopropanol, and (R)-(((1-(6-amino-9H-purin-9-yl)propan-2-yl)oxy)methyl)phosphonic dichloride. [M+H]$^+$ calculated for $C_{24}H_{35}N_6O_5P$: 519.25; found: 519.2.

Example 27

Phenyl N—((S)-1-(1,3-dioxepan-2-yl)propyl)-P—((((R)-1-(6-amino-9H-purin-9-yl)propan-2-yl)oxy)methyl)phosphonamidate (Compound 127)

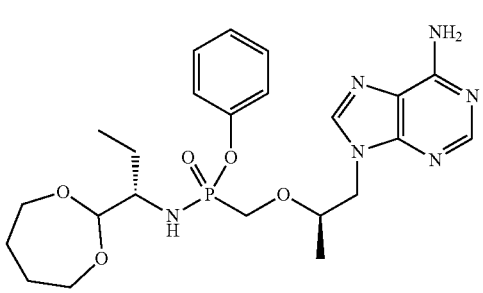 [SMILES: CC[C@H](NP(=O)(CO[C@H](C)Cn1cnc2c(N)ncnc21)Oc1ccccc1)C1OCCCCO1]

Compound 127 was prepared as a mixture of two diastereomers according to Scheme I from phenol, (S)—N-Cbz-2-aminopropanol, and (R)-(((1-(6-amino-9H-purin-9-yl)propan-2-yl)oxy)methyl)phosphonic dichloride. [M+H]$^+$ calculated for $C_{23}H_{33}N_6O_5P$: 505.24; found: 505.2

Example 28

Phenyl P—((((R)-1-(6-amino-9H-purin-9-yl)propan-2-yl)oxy)methyl)-N—((S)-1,1-diethoxypropan-2-yl)phosphonamidate (Compound 128)

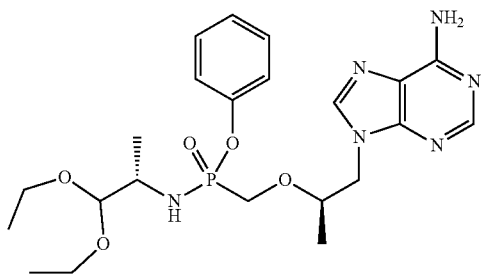 [SMILES: CCOC(OCC)[C@H](C)NP(=O)(CO[C@H](C)Cn1cnc2c(N)ncnc21)Oc1ccccc1]

Compound 128 was prepared as a mixture of two diastereomers according to Scheme I from phenol, (S)—N-Cbz-2-aminopropanol, and (R)-(((1-(6-amino-9H-purin-9-yl)propan-2-yl)oxy)methyl)phosphonic dichloride. [M+H]$^+$ calculated for C$_{22}$H$_{33}$N$_6$O$_5$P: 493.24; found: 493.2.

Example 29

2,3-Dimethylphenyl N—((S)-1-(1,3-dioxan-2-yl)ethyl)-P—((((R)-1-(6-amino-9H-purin-9-yl)propan-2-yl)oxy)methyl)phosphonamidate (Compound 129)

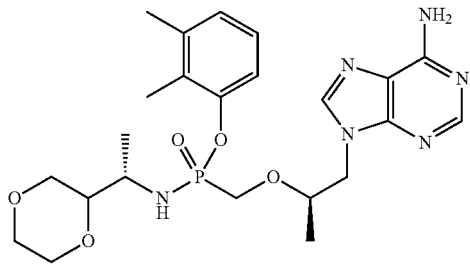 [SMILES: Cc1cccc(OP(=O)(CO[C@H](C)Cn2cnc3c(N)ncnc32)N[C@@H](C)C2COCCO2)c1C]

Compound 129 was prepared as a mixture of two diastereomers according to Scheme I from 2,3-dimethylphenol, (S)—N-Cbz-2-aminopropanol, and (R)-(((1-(6-amino-9H-purin-9-yl)propan-2-yl)oxy)methyl)phosphonic dichloride. [M+H]$^+$ calculated for C$_{23}$H$_{33}$N$_6$O$_5$P: 505.24; found: 505.2.

Example 30

Phenyl P—((((R)-1-(6-amino-9H-purin-9-yl)propan-2-yl)oxy)methyl)-N-((1S)-1-((4S)-4-ethyl-1,3-dioxolan-2-yl)ethyl)phosphonamidate (Compound 130)

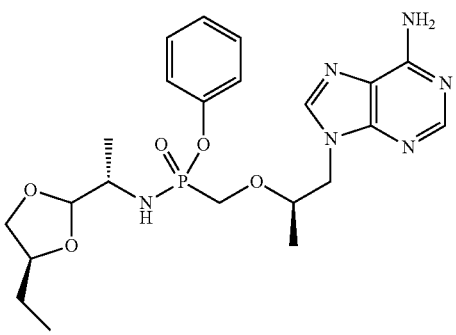 [SMILES: CC[C@H]1COC([C@H](C)NP(=O)(CO[C@H](C)Cn2cnc3c(N)ncnc32)Oc2ccccc2)O1]

Compound 130 was prepared as a mixture of two diastereomers according to Scheme I from phenol, (S)—N-Cbz-2-aminopropanol, and (R)-(((1-(6-amino-9H-purin-9-yl)propan-2-yl)oxy)methyl)phosphonic dichloride. [M+H]$^+$ calculated for C$_{22}$H$_{31}$N$_6$O$_5$P: 491.22; found: 491.2.

Example 31

Phenyl P—((((R)-1-(6-amino-9H-purin-9-yl)propan-2-yl)oxy)methyl)-N-((1S)-1-((4R)-4-ethyl-1,3-dioxolan-2-yl)ethyl)phosphonamidate (Compound 131)

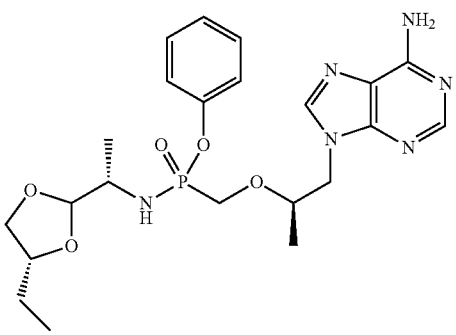 [SMILES: CC[C@@H]1COC([C@H](C)NP(=O)(CO[C@H](C)Cn2cnc3c(N)ncnc32)Oc2ccccc2)O1]

Compound 131 was isolated as a mixture of two diastereomers from the preparation of Compound 114 in Example 14. [M+H]$^+$ calculated for C$_{22}$H$_{31}$N$_6$O$_5$P: 491.22; found: 491.2.

Example 32

1-(1,3-Dioxolan-2-yl)propyl phenyl ((((R)-1-(6-amino-9H-purin-9-yl)propan-2-yl)oxy)methyl)phosphonate (Compound 132)

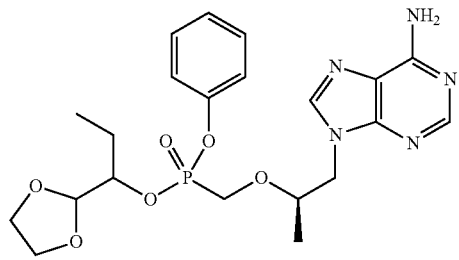 [SMILES: CCC(OP(=O)(CO[C@H](C)Cn1cnc2c(N)ncnc21)Oc1ccccc1)C1OCCO1]

Compound 132 can be prepared as a mixture of four diastereomers according to Scheme I from phenol, 2-hydroxybutanal, and (R)-(((1-(6-amino-9H-purin-9-yl)propan-2-yl)oxy)methyl)phosphonic dichloride.

Example 33

Phenyl (S)—N—((R)-1-(1,3-dioxepan-2-yl)ethyl)-P—((((R)-1-(6-amino-9H-purin-9-yl)propan-2-yl)oxy)methyl)phosphonamidate (Compound 133A) phenyl (R)—N—((R)-1-(1,3-dioxepan-2-yl)ethyl)-P—((((R)-1-(6-amino-9H-purin-9-yl)propan-2-yl)oxy)methyl)phosphonamidate (Compound 133B

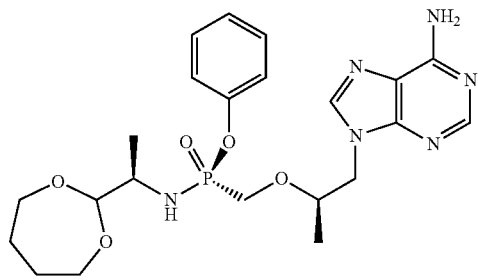

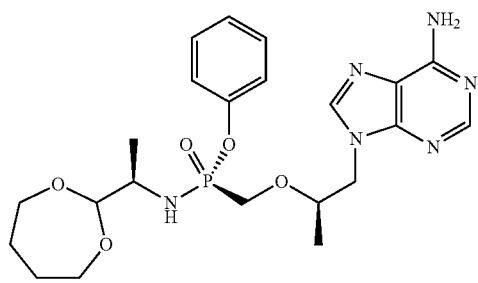

Compounds 133A and 133B were prepared and separated by HPLC according to Scheme I from phenol, (R)—N-Cbz-2-aminopropanol, and (R)-(((1-(6-amino-9H-purin-9-yl)propan-2-yl)oxy)methyl)phosphonic dichloride. [M+H]$^+$ calculated for $C_{22}H_{31}N_6O_5P$: 492.22; found: 492.2.

Example 34

Phenyl (S)—N—((R)-1-(1,3-dioxepan-2-yl)ethyl)-P—((((S)-1-(6-amino-9H-purin-9-yl)propan-2-yl)oxy)methyl)phosphonamidate (Compound 134A) and phenyl (R)—N—((R)-1-(1,3-dioxepan-2-yl)ethyl)-P—((((S)-1-(6-amino-9H-purin-9-yl)propan-2-yl)oxy)methyl)phosphonamidate (Compound 134B)

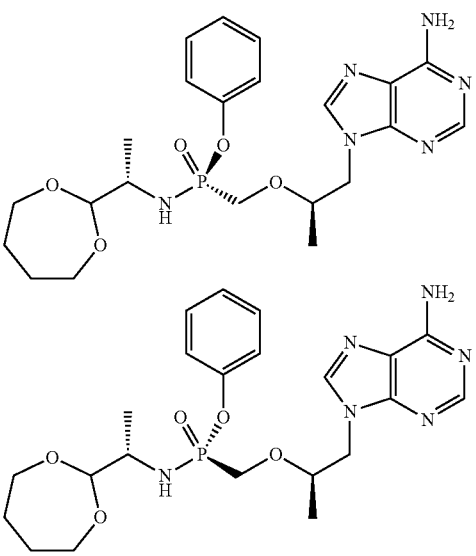

Compounds 134A and 134B were prepared and separated by HPLC according to Scheme I from phenol, (S)—N-Cbz-2-aminopropanol, and (R)-(((1-(6-amino-9H-purin-9-yl)propan-2-yl)oxy)methyl)phosphonic dichloride. [M+H]$^+$ calculated for $C_{22}H_{31}N_6O_5P$: 492.22; found: 492.2.

Example 35

3-Ethylphenyl N—((S)-1-(1,3-dioxan-2-yl)ethyl)-P—((((R)-1-(6-amino-9H-purin-9-yl)propan-2-yl)oxy)methyl)phosphonamidate (Compound 135)

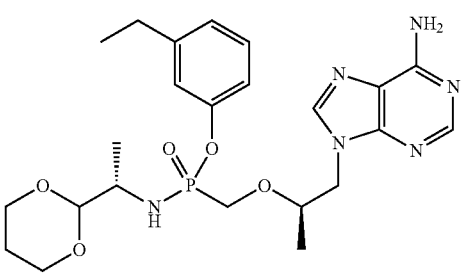 [SMILES: CCc1cccc(OP(=O)(CO[C@H](C)Cn2cnc3c(N)ncnc32)N[C@@H](C)C2OCCCO2)c1]

Compound 135 was prepared as a mixture of two diastereomers according to Scheme I from 3-ethylphenol, (S)—N-Cbz-2-aminopropanol, and (R)-(((1-(6-amino-9H-purin-9-yl)propan-2-yl)oxy)methyl)phosphonic dichloride. [M+H]$^+$ calculated for $C_{23}H_{33}N_6O_5P$: 505.24; found: 505.3.

Example 36

3-Ethylphenyl P—((((R)-1-(6-amino-9H-purin-9-yl)propan-2-yl)oxy)methyl)-N—((S)-1,1-diethoxypropan-2-yl)phosphonamidate (Compound 136)

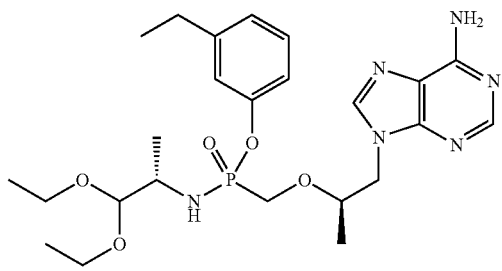 [SMILES: CCOC(OCC)[C@H](C)NP(=O)(CO[C@H](C)Cn1cnc2c(N)ncnc21)Oc1cccc(CC)c1]

Compound was prepared as a mixture of two diastereomers according to Scheme I from 3-ethylphenol, (S)—N-Cbz-2-aminopropanol, and (R)-(((1-(6-amino-9H-purin-9-yl)propan-2-yl)oxy)methyl)phosphonic dichloride. [M+H]$^+$ calculated for $C_{23}H_{33}N_6O_5P$: 521.27; found: 521.2.

Example 37

3-Ethylphenyl P—((((R)-1-(6-amino-9H-purin-9-yl)propan-2-yl)oxy)methyl)-N—((S)-1,1-dimethoxypropan-2-yl)phosphonamidate (Compound 137)

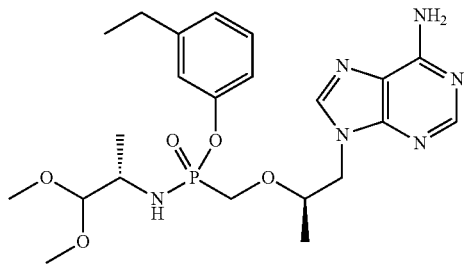 [SMILES: CCc1cccc(OP(=O)(CO[C@H](C)Cn2cnc3c(N)ncnc32)N[C@@H](C)C(OC)OC)c1]

Compound 137 was prepared as a mixture of two diastereomers according to Scheme I from 3-ethylphenol, (S)—N-Cbz-2-aminopropanol, and (R)-(((1-(6-amino-9H-purin-9-yl)propan-2-yl)oxy)methyl)phosphonic dichloride. [M+H]$^+$ calculated for $C_{23}H_{33}N_6O_5P$: 493.23; found: 493.2

Example 38

(2R,3R,5R)-2-((((((S)-1-(1,3-Dioxolan-2-yl)ethyl)amino)(phenoxy)phosphoryl)oxy)methyl)-5-(4-amino-2-oxopyrimidin-1(2H)-yl)-4,4-difluorotetrahydrofuran-3-yl propionate (Compound 138)

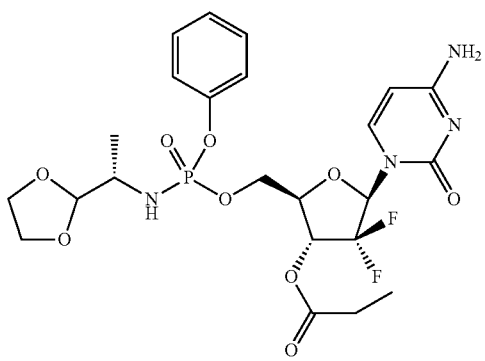

Compound 138 was prepared as a mixture of two diastereomers according to Scheme I from phenol, (S)—N-Cbz-2-aminopropanol, and (2R,3R,5R)-5-(4-amino-2-oxopyrimidin-1(2H)-yl)-4,4-difluoro-2-(hydroxymethyl)tetrahydrofuran-3-yl propionate. [M+H]$^+$ calculated for $C_{23}H_{29}F_2N_4O_9P$: 575.17; found: 575.30.

Example 39

((2R,3R,5R)-5-(4-Butyramido-2-oxopyrimidin-1(2H)-yl)-4,4-difluoro-3-hydroxytetrahydrofuran-2-yl)methyl phenyl (R)—((S)-1-(1,3-dioxolan-2-yl)ethyl)phosphoramidate (Compound 139)

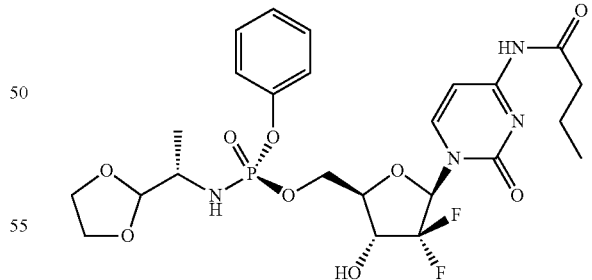

Compound 139 was prepared according to Scheme I from phenol, (S)—N-Cbz-2-aminopropanol, and N-(1-((2R,4R,5R)-3,3-difluoro-4-hydroxy-5-(hydroxymethyl)-tetrahydrofuran-2-yl)-2-oxo-1,2-dihydropyrimidin-4-yl)butyramide. [M+H]$^+$ calculated for $C_{24}H_{31}F_2N_4O_9P$: 589.19; found: 589.35.

Example 40

((2R,3R,5R)-5-(4-Butyramido-2-oxopyrimidin-1 (2H)-yl)-4,4-difluoro-3-hydroxytetrahydrofuran-2-yl)methyl phenyl (S)—((S)-1-(1,3-dioxolan-2-yl) ethyl)phosphoramidate (Compound 140)

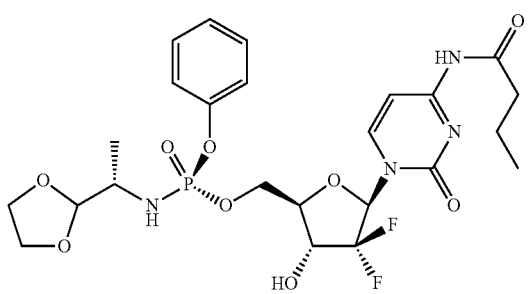

Compound 140 was isolated as a minor isomer from the preparation of Compound 131 in Example 31. [M+H]$^+$ calculated for $C_{24}H_{31}F_2N_4O_9P$: 589.19; found: 589.30.

Example 41

(2S)-2-(((((R)-1-(6-Amino-9H-purin-9-yl)propan-2-yl)oxy)methyl)(phenoxyphosphoryl)amino)propyl propionate (Compound 141)

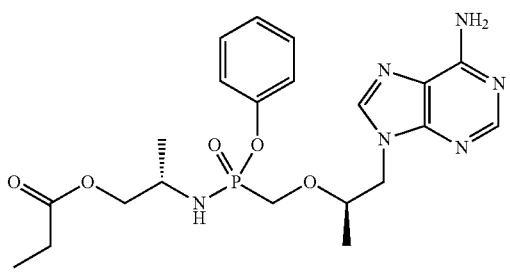 [SMILES: CCC(=O)OC[C@H](C)NP(=O)(CO[C@H](C)Cn1cnc2c(N)ncnc21)Oc1ccccc1]

Compound 141 was prepared as a mixture of two diastereomers according to Scheme I from phenol, (S)-2-aminopropanol, and (R)-(((1-(6-amino-9H-purin-9-yl)propan-2-yl)oxy)methyl)phosphonic dichloride. [M+H]$^+$ calculated for $C_{21}H_{29}N_6O_5P$: 477.20; found: 477.2.

Example 42

3-((((((R)-1-(6-Amino-9H-purin-9-yl)propan-2-yl)oxy)methyl)(phenoxy)phosphoryl)amino)butyl acetate (Compound 142)

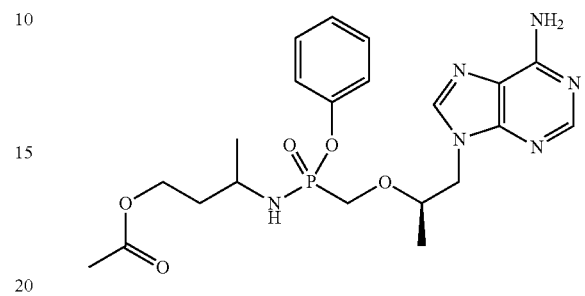

Compound 142 was prepared as a mixture of four diastereomers according to Scheme I from phenol, 3-aminobutanol, and (R)-(((1-(6-amino-9H-purin-9-yl)propan-2-yl)oxy)methyl)phosphonic dichloride. [M+H]$^+$ calculated for $C_{21}H_{29}N_6O_5P$: 477.20; found: 477.1.

Example 43

3-Ethylphenyl P—((((R)-1-(6-amino-9H-purin-9-yl)propan-2-yl)oxy)methyl)-N-(2,2-diethoxyethyl)phosphonamidate (Compound 143)

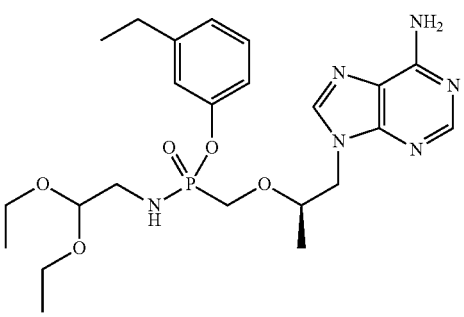 [SMILES: CCOC(CNP(=O)(CO[C@H](C)Cn1cnc2c(N)ncnc21)Oc1cccc(CC)c1)OCC]

Compound 143 was prepared as a mixture of two diastereomers according to Scheme I from 3-ethylphenol, 2-aminoethanol, and (R)-(((1-(6-amino-9H-purin-9-yl)propan-2-yl)oxy)methyl)phosphonic dichloride. [M+H]$^+$ calculated for $C_{23}H_{35}N_6O_5P$: 507.25; found: 507.2.

Example 44

Phenyl P—((((R)-1-(6-amino-9H-purin-9-yl)propan-2-yl)oxy)methyl)-N—((S)-1,1-dipropoxypropan-2-yl)phosphonamidate (Compound 144)

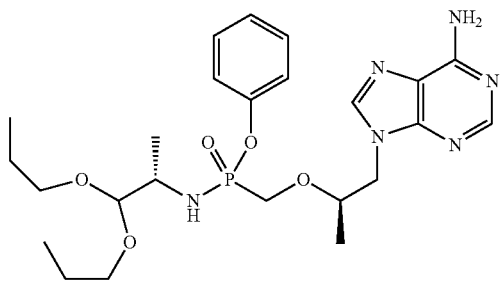 [SMILES: CCCOC(OCCC)[C@H](C)NP(=O)(CO[C@H](C)Cn1cnc2c(N)ncnc21)Oc1ccccc1]

Compound 144 was prepared as a mixture of two diastereomers according to Scheme I from phenol, (S)—N-Cbz-2-aminopropanol, and (R)-(((1-(6-amino-9H-purin-9-yl)propan-2-yl)oxy)methyl)phosphonic dichloride. [M+H]$^+$ calculated for $C_{24}H_{37}N_6O_5P$: 521.27; found: 521.2.

Example 45

Phenyl P—((((R)-1-(6-amino-9H-purin-9-yl)propan-2-yl)oxy)methyl)-N—((S)-1,1-dibutoxypropan-2-yl)phosphonamidate (Compound 45)

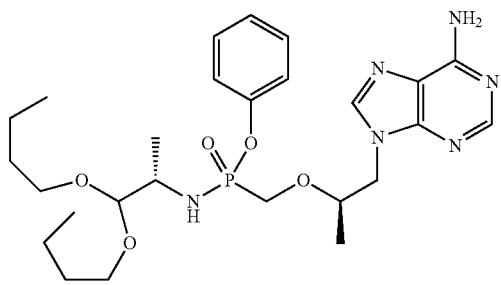 [SMILES: CCCCOC(OCCCC)[C@H](C)NP(=O)(CO[C@H](C)Cn1cnc2c(N)ncnc21)Oc1ccccc1]

Compound 145 was prepared as a mixture of two diastereomers according to Scheme I from phenol, (S)—N-Cbz-2-aminopropanol, and (R)-(((1-(6-amino-9H-purin-9-yl)propan-2-yl)oxy)methyl)phosphonic dichloride. [M+H]$^+$ calculated for $C_{26}H_{41}N_6O_5P$: 549.30; found: 549.3.

Example 46

Phenyl P—((((R)-1-(6-amino-9H-purin-9-yl)propan-2-yl)oxy)methyl)-N-(2,2-dibutoxyethyl)phosphonamidate (Compound 146)

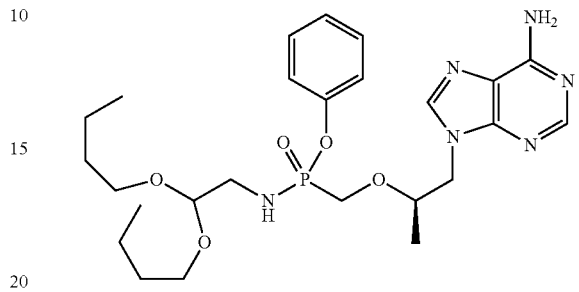

Compound 146 was prepared as a mixture of two diastereomers according to Scheme I from phenol, (S)—N-Cbz-2-aminopropanol, and (R)-(((1-(6-amino-9H-purin-9-yl)propan-2-yl)oxy)methyl)phosphonic dichloride. [M+H]$^+$ calculated for $C_{25}H_{39}N_6O_5P$: 535.28; found: 535.3.

Example 47

Phenyl P—((((R)-1-(6-amino-9H-purin-9-yl)propan-2-yl)oxy)methyl)-N-(2,2-dipropoxyethyl)phosphonamidate (Compound 147)

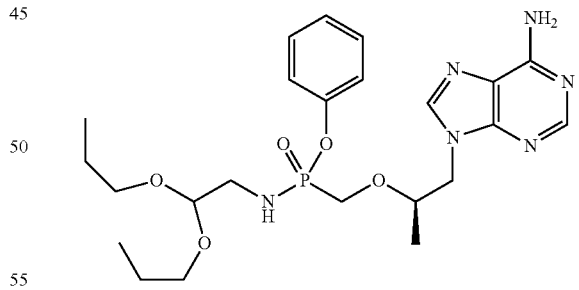

Compound 147 was prepared as a mixture of two diastereomers according to Scheme I from phenol, 2-aminoethanol, and (R)-(((1-(6-amino-9H-purin-9-yl)propan-2-yl)oxy)methyl)phosphonic dichloride. [M+H]$^+$ calculated for $C_{23}H_{35}N_6O_5P$: 507.25; found: 507.2.

Example 48

(2R,3R,4R,5R)-2-(((((2,2-Diethoxyethyl)amino)(phenoxy)phosphoryl)oxy)methyl)-5-(2,4-dioxo-3,4-dihydropyrimidin-1(2H)-yl)-4-fluoro-4-methyltetrahydrofuran-3-yl propionate (Compound 148)

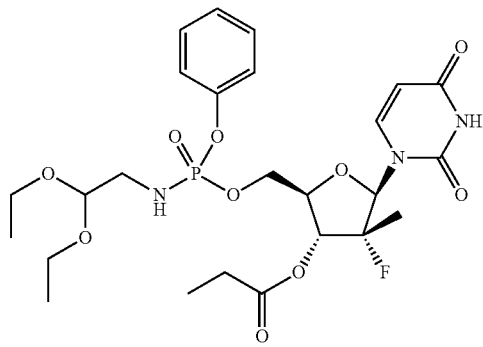 [SMILES: CCOC(CNP(=O)(OC[C@H]1O[C@@H](n2ccc(=O)[nH]c2=O)[C@](C)(F)[C@@H]1OC(=O)CC)Oc1ccccc1)OCC]

Compound 148 was prepared as a mixture of two diastereomers according to Scheme I from phenol, 2-aminoethanol, and (R)-(((1-(6-amino-9H-purin-9-yl)propan-2-yl)oxy)methyl)phosphonic dichloride. [M−H]⁺ calculated for $C_{25}H_{35}FN_3O_{10}P$: 586.2; found: 586.4.

Example 49

(2S)-2-((((((R)-1-(6-Amino-9H-purin-9-yl)propan-2-yl)oxy)methyl)(phenoxy)phosphoryl)amino)propyl 2,2-dimethylpropionate (Compound 149)

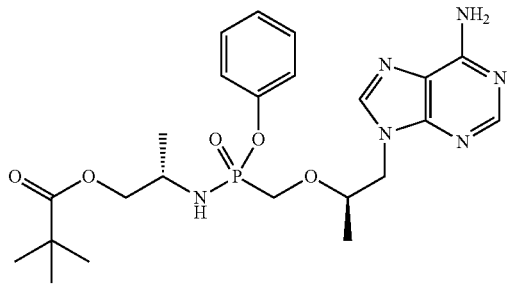 [SMILES: C[C@H](Cn1cnc2c(N)ncnc21)OCP(=O)(N[C@@H](C)COC(=O)C(C)(C)C)Oc1ccccc1]

Compound 149 was prepared as a mixture of two diastereomers according to Scheme I from phenol, (S)-2-aminopropanol, and (R)-(((1-(6-amino-9H-purin-9-yl)propan-2-yl)oxy)methyl)phosphonic dichloride. [M+H]⁺ calculated for $C_{23}H_{33}N_6O_5P$: 505.24; found: 505.2.

Example 50

(2R,3S,5R)-2-((((((S)-1,1-Diethoxypropan-2-yl)amino)(phenoxy)phosphoryl)oxy)methyl)-5-(5-fluoro-2,4-dioxo-3,4-dihydropyrimidin-1(2H)-yl)tetrahydrofuran-3-yl propionate (Compound 150)

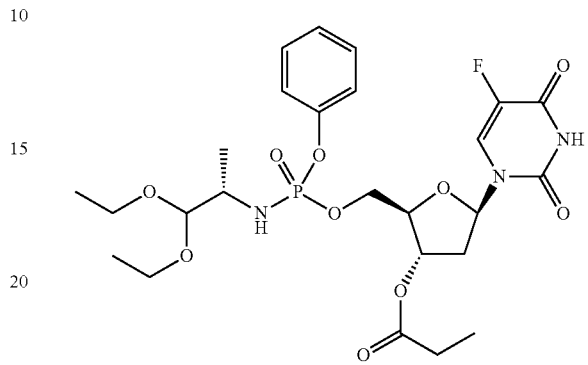

Compound 150 was prepared as a mixture of two diastereomers according to Scheme I from phenol, (S)—N-Cbz-2-aminopropanol, and 5-fluoro-((2R,4S,5R)-4-hydroxy-5-(hydroxymethyl)tetrahydrofuran-2-yl)pyrimidine-2,4(1H,3H)-dione. [M−H]⁺ calculated for $C_{25}H_{35}FN_3O_{10}P$: 586.2; found: 586.1.

Example 51

((2R,3S,5R)-5-(5-Fluoro-2,4-dioxo-3,4-dihydropyrimidin-1(2H)-yl)-3-hydroxytetrahydrofuran-2-yl)methyl phenyl ((S)-1,1-dipropoxypropan-2-yl)phosphoramidate (Compound 151)

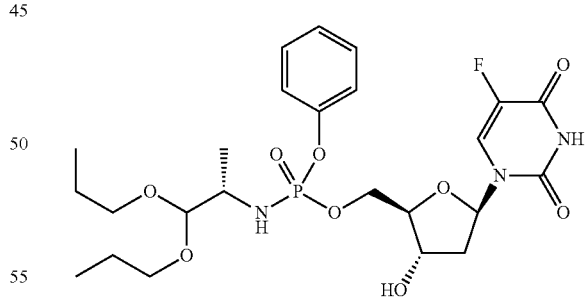

Compound 151 was prepared as a mixture of two diastereomers according to Scheme I from phenol, (S)—N-Cbz-2-aminopropanol, and 5-fluoro-((2R,4S,5R)-4-hydroxy-5-(hydroxymethyl)tetrahydrofuran-2-yl)pyrimidine-2,4(1H,3H)-dione. [M−H]-calculated for $C_{24}H_{35}FN_3O_9P$: 558.2; found: 558.0.

Example 52

(2R,3S,5R)-2-((((((S)-1,1-Dipropoxypropan-2-yl)amino)(phenoxy)phosphoryl)oxy)methyl)-5-(5-fluoro-2,4-dioxo-3,4-dihydropyrimidin-1(2H)-yl)tetrahydrofuran-3-yl propionate (Compound 152)

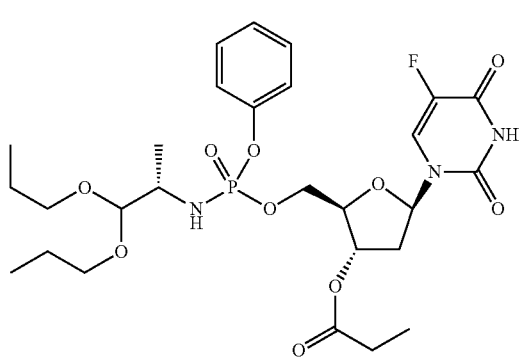 [SMILES: CCCOC(OCCC)[C@H](C)NP(=O)(OC[C@H]1O[C@@H](n2cc(F)c(=O)[nH]c2=O)C[C@@H]1OC(=O)CC)Oc1ccccc1]

Compound 152 was prepared as a mixture of two diastereomers according to Scheme I from phenol, (S)—N-Cbz-2-aminopropanol, and 5-fluoro-((2R,4S,5R)-4-hydroxy-5-(hydroxymethyl)tetrahydrofuran-2-yl)pyrimidine-2,4(1H, 3H)-dione. [M–H]−calculated for $C_{27}H_{39}FN_3O_{10}O_{10}P$: 614.23; found: 614.2.

Example 53

(2R,3S,5R)-2-((((((S)-1,1-Diethoxypropan-2-yl)amino)(phenoxy)phosphoryl)oxy)methyl)-5-(5-fluoro-2,4-dioxo-3,4-dihydropyrimidin-1(2H)-yl)tetrahydrofuran-3-yl 2,2-dimethylpropionate (Compound 153)

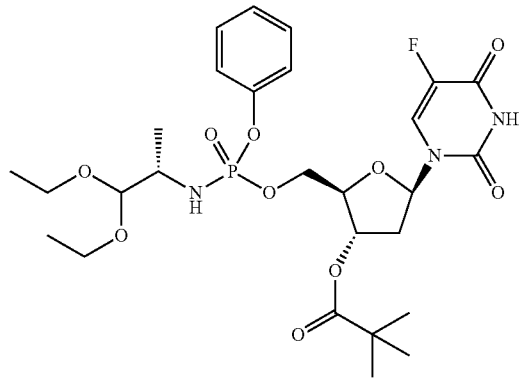 [SMILES: CCOC(OCC)[C@H](C)NP(=O)(OC[C@H]1O[C@@H](n2cc(F)c(=O)[nH]c2=O)C[C@@H]1OC(=O)C(C)(C)C)Oc1ccccc1]

Compound 153 was prepared as a mixture of two diastereomers according to Scheme I from phenol, (S)—N-Cbz-2-aminopropanol, and 5-fluoro-1-((2R,4S,5R)-4-hydroxy-5-(hydroxymethyl)tetrahydrofuran-2-yl)pyrimidine-2,4(1H, 3H)-dione. [M–H]+ calculated for $C_{27}H_{39}FN_3O_{10}P$: 614.23; found: 614.2.

Example 54

Phenyl P—((((R)-1-(6-amino-9H-purin-9-yl)propan-2-yl)oxy)methyl)-N—((S)-1,1-diisopropoxypropan-2-yl)phosphonamidate (Compound 154)

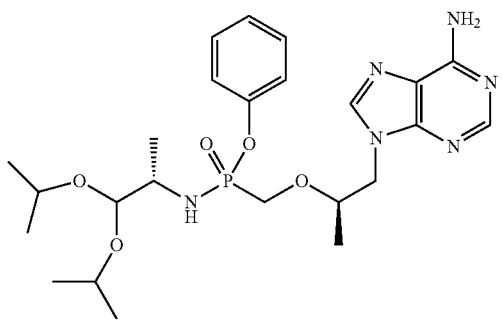 [SMILES: CC(C)OC(OC(C)C)[C@H](C)NP(=O)(CO[C@H](C)Cn1cnc2c(N)ncnc21)Oc1ccccc1]

Compound 154 was prepared as a mixture of two diastereomers according to Scheme I from phenol, (S)—N-Cbz-2-aminopropanol, and 5-fluoro-1-((2R,4S,5R)-4-hydroxy-5-(hydroxymethyl)tetrahydrofuran-2-yl)pyrimidine-2,4(1H, 3H)-dione. [M–H]+ calculated for $C_{24}H_{37}N_6O_5P$: 520.26; found: 521.2.

Example 55

Phenyl (S)—P—((((R)-1-(6-amino-9H-purin-9-yl)propan-2-yl)oxy)methyl)-N—((S)-1,1-dipropoxypropan-2-yl)phosphonamidate (Compound 155)

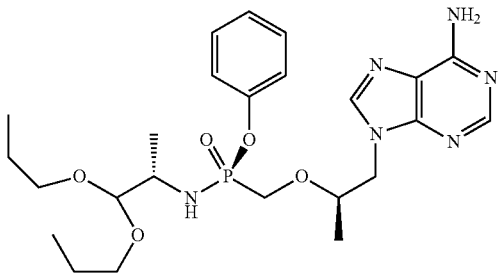 [SMILES: CCCOC(OCCC)[C@H](C)N[P@](=O)(CO[C@H](C)Cn1cnc2c(N)ncnc21)Oc1ccccc1]

Compound 155 was isolated via chiral HPLC from a mixture of two diastereomers (Compound 144).

Example 56

Phenyl (R)—P—((((R)-1-(6-amino-9H-purin-9-yl)propan-2-yl)oxy)methyl)-N—((S)-1,1-dipropoxypropan-2-yl)phosphonamidate (Compound 156)

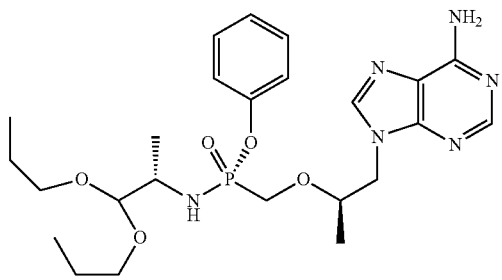 [SMILES: CCCOC(OCCC)[C@H](C)N[P@@](=O)(CO[C@H](C)Cn1cnc2c(N)ncnc21)Oc1ccccc1]

Compound 156 was isolated via chiral HPLC from a mixture of two diastereomers (Compound 144).

Example 57

(2R,3S,5R)-2-((((((S)-1,1-Dimethoxypropan-2-yl)amino)(3-ethylphenoxy)phosphoryl)oxy)methyl)-5-(5-fluoro-2,4-dioxo-3,4-dihydropyrimidin-1(2H)-yl)tetrahydrofuran-3-yl propionate (Compound 157)

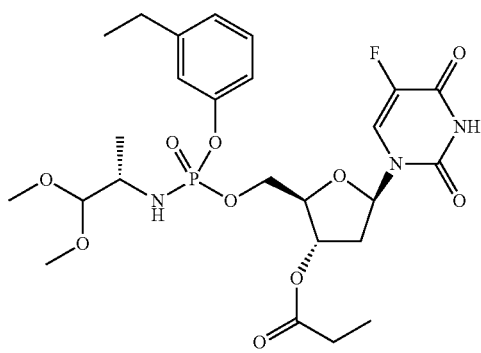 [SMILES: CCC(=O)O[C@H]1C[C@H](n2cc(F)c(=O)[nH]c2=O)O[C@@H]1COP(=O)(N[C@@H](C)C(OC)OC)Oc1cccc(CC)c1]

Compound 157 was prepared as a mixture of two diastereomers according to Scheme I from 3-ethylphenol, (S)—N-Cbz-2-aminopropanol, and 5-fluoro-1-((2R,4S,5R)-4-hydroxy-5-(hydroxymethyl)tetrahydrofuran-2-yl)pyrimidine-2,4(1H,3H)-dione. [M−H]-calculated for $C_{25}H_{35}FN_3O_1O_5P$: 586.19; found: 586.2.

Example 58

(2R,3S,5R)-2-((((((S)-1,1-Dimethoxypropan-2-yl)amino)(phenoxy)phosphoryl)oxy)methyl)-5-(5-fluoro-2,4-dioxo-3,4-dihydropyrimidin-1(2H)-yl)tetrahydrofuran-3-yl propionate (Compound 158)

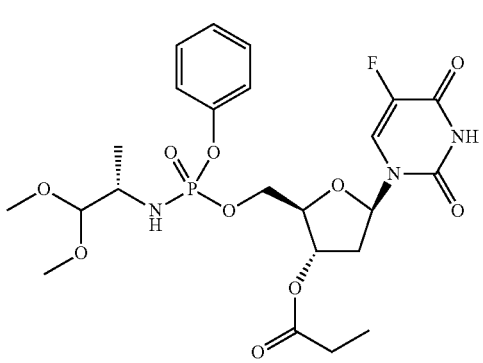 [SMILES: CCC(=O)O[C@H]1C[C@H](n2cc(F)c(=O)[nH]c2=O)O[C@@H]1COP(=O)(N[C@@H](C)C(OC)OC)Oc1ccccc1]

Compound 158 was prepared as a mixture of two diastereomers according to Scheme I from phenol, (S)—N-Cbz-2-aminopropanol, and 5-fluoro-((2R,4S,5R)-4-hydroxy-5-(hydroxymethyl)tetrahydrofuran-2-yl)pyrimidine-2,4(1H, 3H)-dione. [M−H]-calculated for $C_{23}H_{31}FN_3O_{10}P$: 558.16; found: 558.2.

Example 59

(2R,3S,5R)-2-(((((2,2-Dimethoxyethyl)amino)(phenoxy)phosphoryl)oxy)methyl)-5-(5-fluoro-2,4-dioxo-3,4-dihydropyrimidin-1(2H)-yl)tetrahydrofuran-3-yl propionate (Compound 159)

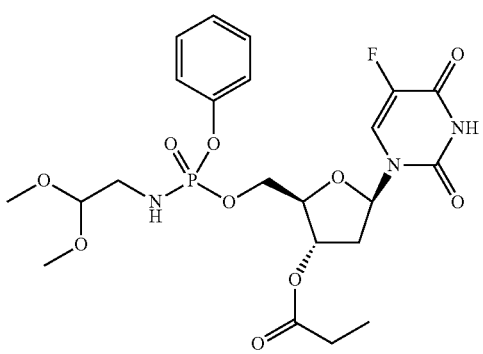 [SMILES: CCC(=O)O[C@H]1C[C@H](n2cc(F)c(=O)[nH]c2=O)O[C@@H]1COP(=O)(NCC(OC)OC)Oc1ccccc1]

Compound 159 was prepared as a mixture of two diastereomers according to Scheme I from phenol, N-Cbz-2-aminoethanol, and 5-fluoro-1-((2R,4S,5R)-4-hydroxy-5-(hydroxymethyl)tetrahydrofuran-2-yl)pyrimidine-2,4(1H, 3H)-dione. $^1$H-NMR (400 MHz, CDCl$_3$) 7.88 (d, J=6.0, 1H), 7.81 (d, J=6.0, 1H), 7.46-7.15 (m, 12H), 6.33-6.20 (m, 2H), 5.30 (m, 2H).

Example 60

(2R,3S,5R)-2-((((((S)-1-(1,3-Dioxolan-2-yl)ethyl)amino)(phenoxy)phosphoryl)oxy)methyl)-5-(5-fluoro-2,4-dioxo-3,4-dihydropyrimidin-1(2H)-yl)tetrahydrofuran-3-yl propionate (Compound 160)

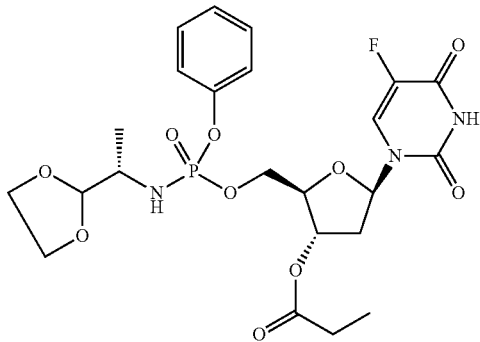 [SMILES: CCC(=O)O[C@H]1C[C@H](n2cc(F)c(=O)[nH]c2=O)O[C@@H]1COP(=O)(N[C@@H](C)C1OCCO1)Oc1ccccc1]

Compound 160 was prepared as a mixture of two diastereomers according to Scheme I from phenol, (S)—N-Cbz-2-aminopropanol, and 5-fluoro-1-((2R,4S,5R)-4-hydroxy-5-(hydroxymethyl)tetrahydrofuran-2-yl)pyrimidine-2,4(1H,3H)-dione. $[M+H]^+$ calculated for $C_{23}H_{29}FN_3O_{10}P$: 558.17; found: 558.2.

Example 61

(2R,3S,5R)-2-((((((S)-1,1-Dimethoxypropan-2-yl)amino)(phenoxy)phosphoryl)oxy)methyl)-5-(4-ethoxy-5-fluoro-2-oxopyrimidin-1(2H)-yl)tetrahydrofuran-3-yl propionate (Compound 161)

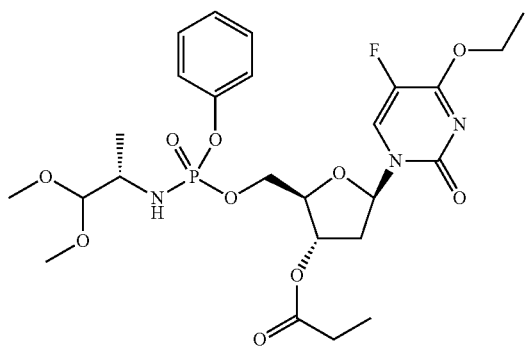 [SMILES: CCOc1nc(=O)n([C@H]2C[C@H](OC(=O)CC)[C@@H](COP(=O)(N[C@@H](C)C(OC)OC)Oc3ccccc3)O2)cc1F]

Compound 161 was prepared as a mixture of two diastereomers according to Scheme I from phenol, (S)—N-Cbz-2-aminopropanol, and (2R,3S,5R)-5-(4-ethoxy-5-fluoro-2-oxopyrimidin-1(2H)-yl)-2-(hydroxymethyl)tetrahydrofuran-3-yl propionate. $^1$H-NMR (400 MHz, CDCl$_3$) 8.00 (d, J=6.0, 1H), 7.95 (d, J=5.6, 1H), 7.40-7.10 (m, 12H), 6.33-6.18 (m, 2H), 5.27 (m, 2H).

BIOLOGICAL EXAMPLES

Examples of use of the method include the following. It will be understood that the following are examples and that the method is not limited solely to these examples.

Example A: Tissue Distribution Following Oral Administration of Reference Compounds and the Disclosed Compounds The liver specificity of the disclosed compounds is compared relative to a corresponding active compound in liver and other organs that could be targets of toxicity.

Methods:

Reference compounds and the phosphor(n)amidatacetal and phosph(on)atacetal compounds are administered at 5-20 mg/kg to fasted rats by oral gavage. Plasma concentrations of the active, metabolite, and phosphor(n)amidatacetal and phosph(on)atacetal compounds in circulation and in the hepatic portal vein are determined by HPLC-UV, and the liver, small intestine, and other organ concentrations are measured by LC-MS using the standard chromatography method.

Results:

Table 3 provides the results of selected new compounds, which demonstrate the liver targeting of the phosphor(n)amidatacetal and phosph(on)atacetal compounds and provide evidence for improved efficiency of the compounds over other types of compounds in liver-targeting and achieving high level of the active in the liver. This can occur solely by the high efficiency liver targeting provided by the phosphor(n)amidatacetal and phosph(on)atacetal compound.

TABLE 3

Nucleoside triphosphate levels in the liver and nucleotide level in blood after oral administration of selected compounds at 5 mg/kg oral dose in rats

| Compound | NTP$_{liver}$ (ng/g) | Nuc$_{blood}$ (ng/mL) | NTP/Nuc |
|---|---|---|---|
| 116 | <1,000 | <20 | >50 |
| 119 | >1,000 | <20 | >50 |
| 122 | >1,000 | >20 | >50 |
| 126 | >1,000 | >20 | >50 |
| 130 | <1,000 | >20 | <50 |
| 133A | >1,000 | <20 | >50 |
| 134B | >1,000 | >20 | >50 |
| 137 | >1,000 | >20 | >50 |
| 143 | >1,000 | <20 | >50 |
| 144 | >1,000 | >20 | >50 |
| 146 | >1,000 | <20 | >50 |
| 155 | >1,000 | >20 | >50 |
| 156 | >1,000 | >20 | >50 |

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15%, 10%, 5%, 3%, 1%, 0.1%, or otherwise. Similarly, in certain embodiments, the terms "generally perpendicular" and "substantially perpendicular" refer to a value, amount, or characteristic that departs from exactly perpendicular by less than or equal to 15%, 10%, 5%, 3%, 1%, 0.1%, or otherwise.

The above description discloses several methods and materials. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

Although the invention has been described with reference to embodiments and examples, it should be understood that numerous and various modifications can be made without departing from the spirit of the invention. Accordingly, the invention is limited only by the following claims.

What is claimed is:
1. A compound of Formula IVa:

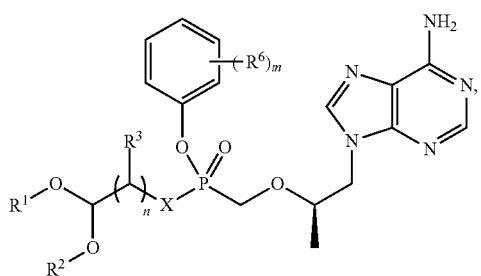

or a stereoisomer or a pharmaceutically acceptable salt thereof
wherein:
$R^1$ and $R^2$ are independently selected from the group consisting of an optionally substituted $C_1$-$C_6$ alkyl, an optionally substituted $C_6$-$C_{10}$ aryl, and an optionally substituted 5- to 10-membered heteroaryl; or alternatively, $R^1$ and $R^2$ together with the atoms to which they are attached form a four to ten membered heterocycle optionally substituted with a $C_1$-$C_6$ alkyl;
each $R^3$ is independently selected from the group consisting of hydrogen, an optionally substituted $C_1$-$C_6$ alkyl, an optionally substituted $C_7$-$C_{16}$ arylalkyl, and an optionally substituted 5- to 10-membered heteroaryl ($C_1$-$C_6$)alkyl;

each $R^6$ is independently selected from halogen, an optionally substituted $C_1$-$C_6$ alkyl, and an optionally substituted $C_1$-$C_6$ alkyloxy;
m is 0, 1, 2, or 3;
n is 1 or 2; and
X is O (oxygen) or NH.
2. The compound of claim 1, wherein each $R^3$ is independently an optionally substituted $C_1$-$C_6$ alkyl.
3. The compound of claim 1, wherein m is 0, 1, or 2.
4. The compound of claim 1, wherein n is 1.
5. The compound of claim 1, wherein X is NH.
6. The compound of claim 1, wherein $R^3$ is hydrogen or $C_1$-$C_6$ alkyl.
7. The compound of claim 1, wherein $R^6$ is $C_1$-$C_6$ alkyl; and m is 1, 2, or 3.
8. The compound of claim 1, wherein the compound is selected from the group consisting of:

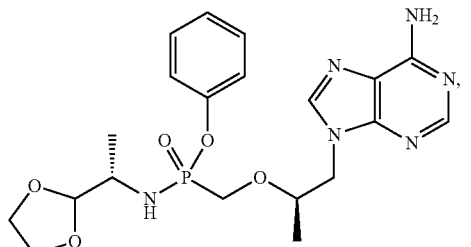

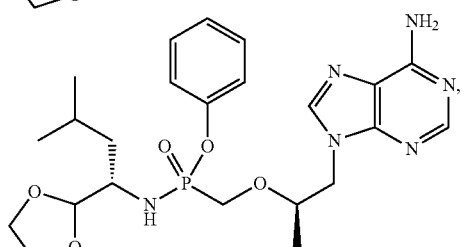

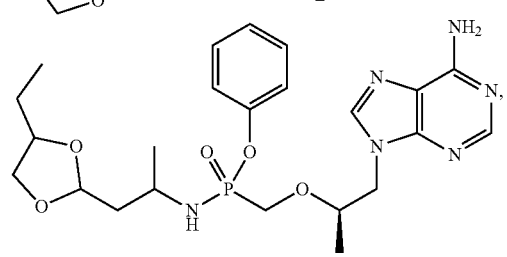

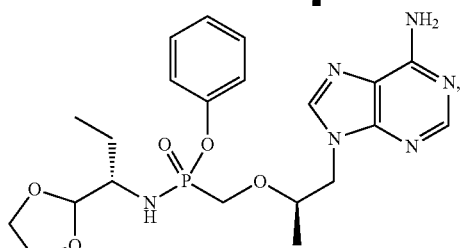

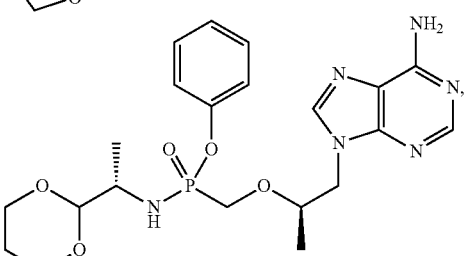

63
-continued
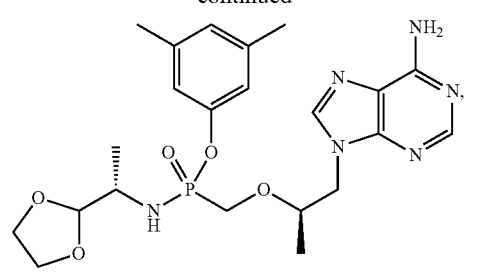
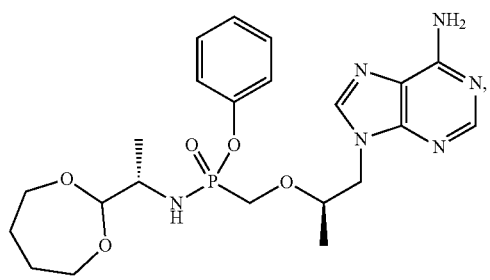
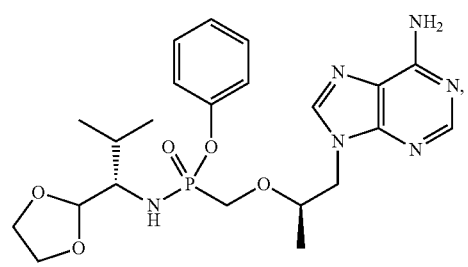
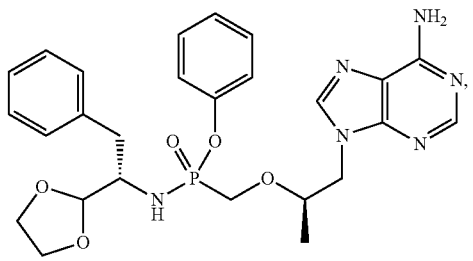
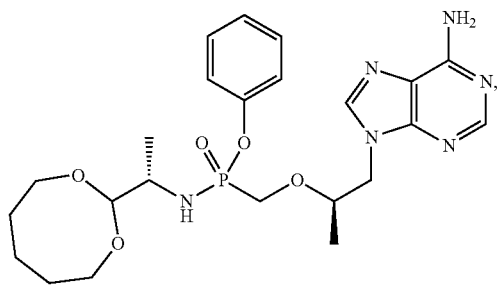
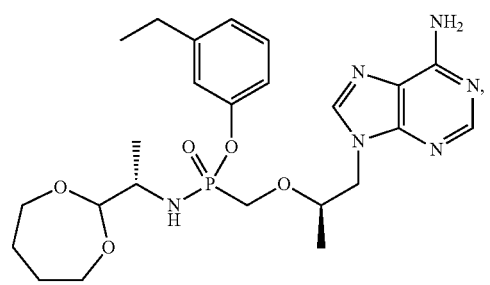
64
-continued
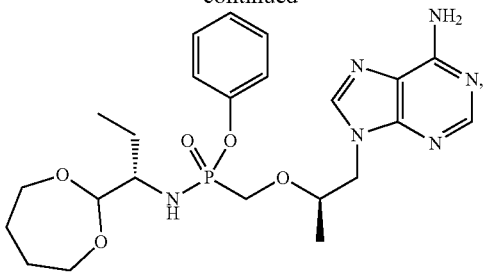
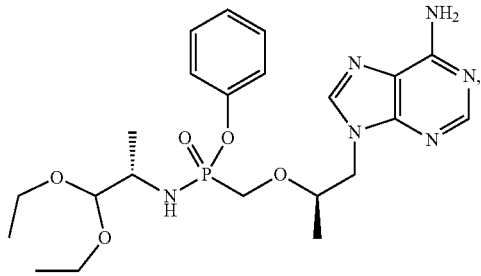
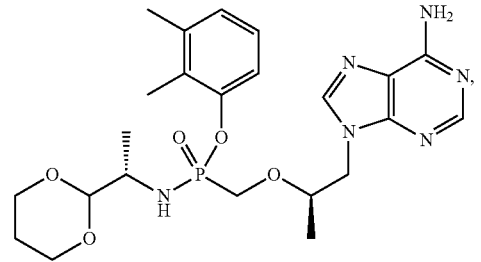
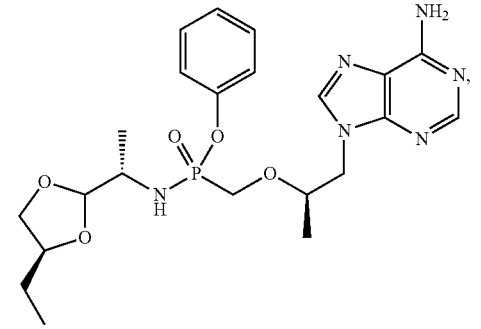
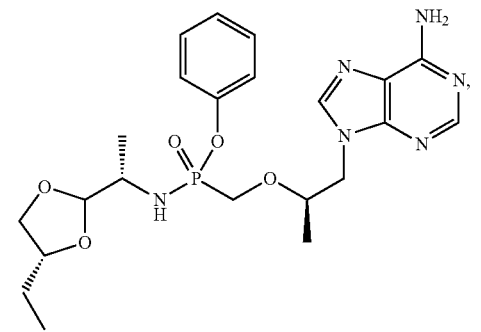
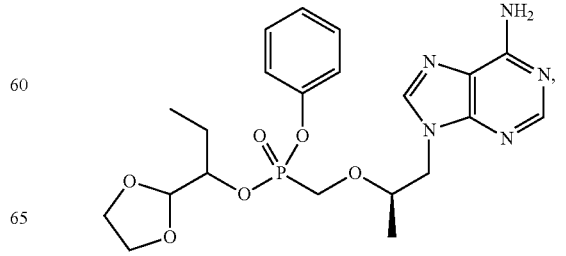

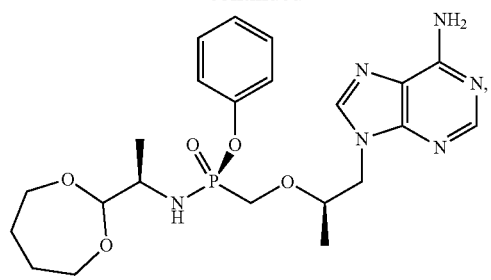
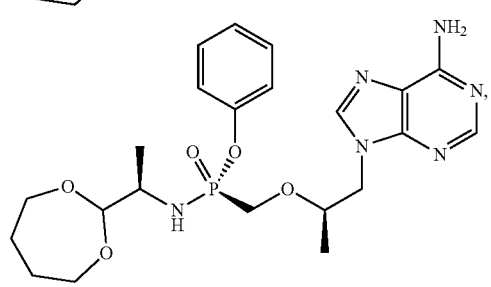
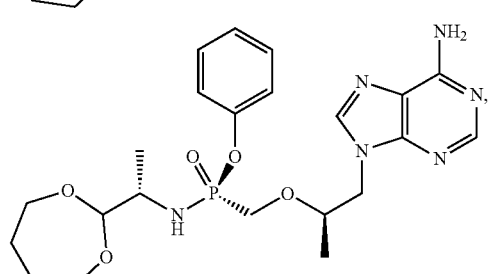
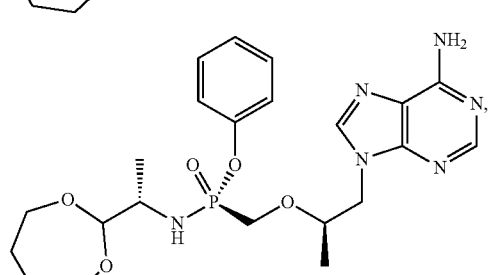
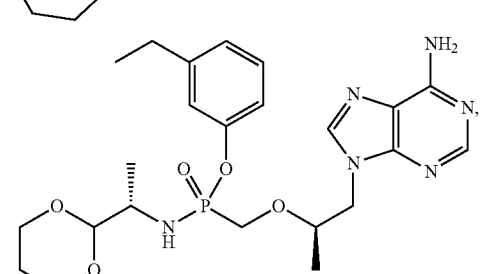
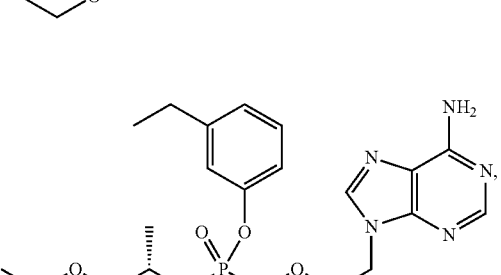
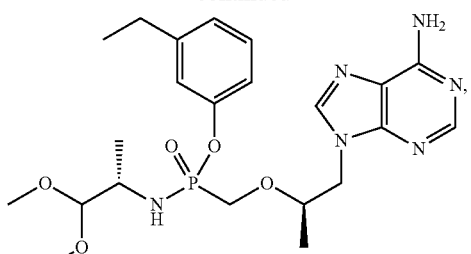
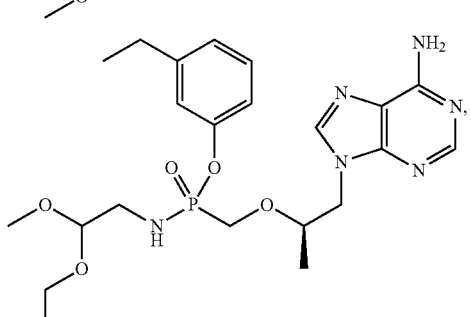
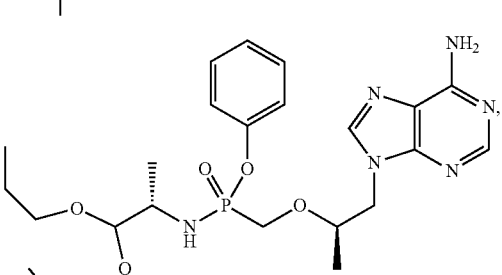
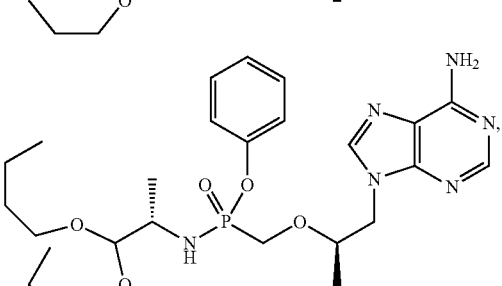
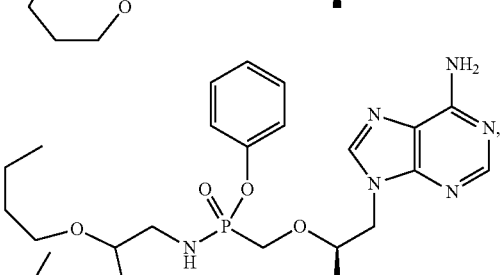
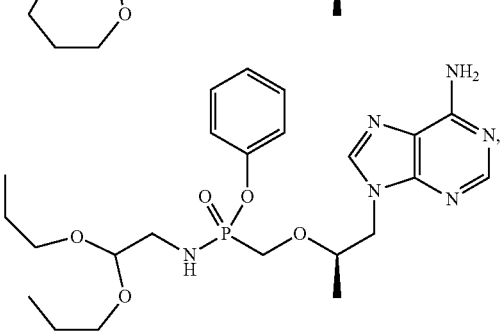

-continued

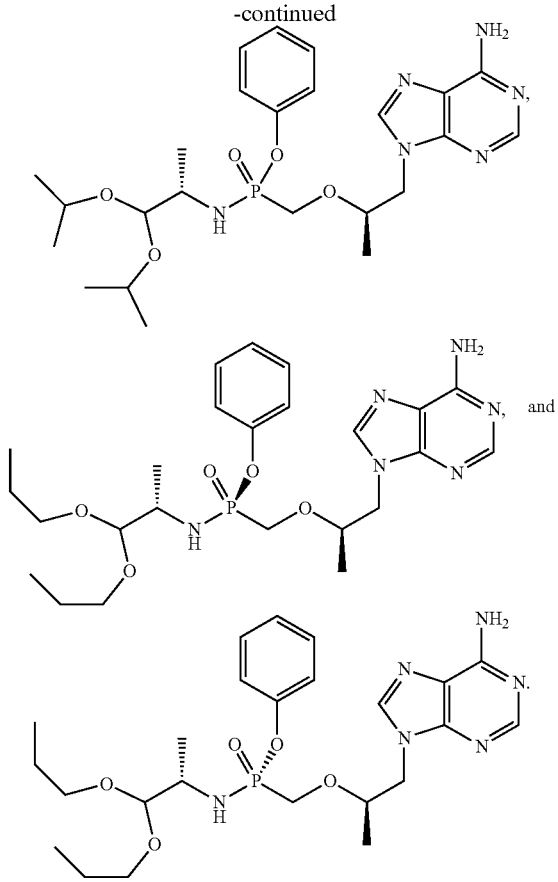

and

9. A pharmaceutical composition comprising the compound of claim 1 and a pharmaceutically acceptable excipient.

10. The pharmaceutical composition of claim 9, further comprising one or more of cobicistat, emtricitabine and elvitegravir.

11. The pharmaceutical composition of claim 9, further comprising one or more of ribavirin, peginterferon-alfa, simeprevir, ledipasvir, or daclatasvir.

12. A method of treating hepatitis or viral infection, comprising administering an effective amount of the compound of claim 1 to a subject in need thereof.

13. The method of claim 12, further comprising administering an effective amount of at least one additional therapeutic agent to the subject in need thereof.

14. The method of claim 12, wherein the subject is a mammal.

15. The method of claim 12, wherein the subject is human.

16. A method of inhibiting viral replication in a cell comprising contacting the cell with the compound of claim 1.

17. A composition comprising a compound of claim 1 for use in treating a viral infection in a subject.

18. The composition of claim 17, in combination with one or more additional therapeutic agents.

19. The composition of claim 18, wherein the additional therapeutic agents are selected from the group consisting of thymosin alpha-1, interferon-λ, an inhibitor of HCV protease, an inhibitor of HCV NS5A replication complex, an inhibitor of HCV NS5B polymerase, an inhibitor of HCV helicase, a cyclophilin inhibitor, an inhibitor of inosine monophosphate dehydrogenase, ribavirin, interferon-α, and pegylated interferon-α.

20. The composition of claim 18, wherein the additional therapeutic agents comprise a direct-acting antiviral agent.

21. The composition of claim 20, wherein the direct-acting antiviral agent is selected from the group consisting of an inhibitor of HCV protease, an inhibitor of HCV NS5A replication complex, a nucleoside-based inhibitor of HCV NS5B polymerase, a non-nucleoside inhibitor of HCV NS5B polymerase, and an inhibitor of HCV helicase.

22. The composition of claim 18, wherein the additional therapeutic agents are selected for HBV treatment from the group consisting of: a HBV entry inhibitor, a HBV cccDNA inhibitor, a HBV capsid inhibitor, an interferon, and a HBV assembly inhibitor.

23. The composition of claim 18, wherein the additional therapeutic agents are selected from the group consisting of: sorafenib, regorafenib, and a PD-1 or PD-L1 checkpoint inhibitor.

24. The composition of claim 18, wherein the additional therapeutic agents are selected for HIV treatment from the group of non-nucleoside reverse transcriptase inhibitors, other nucleoside analog reverse transcriptase inhibitors, and protease inhibitors.

* * * * *

UNITED STATES PATENT AND TRADEMARK OFFICE
CERTIFICATE OF CORRECTION

PATENT NO. : 12,110,308 B2
APPLICATION NO. : 16/960819
DATED : October 8, 2024
INVENTOR(S) : Lin Zhi It is certified that error appears in the above-identified patent and that said Letters Patent is hereby corrected as shown below:

On the Title Page

Column 2, Line 1, item (57) delete "are phosphor (n) amidatacetal and" and insert -- are phosphor(n)amidatacetal and --.

Column 2, Line 1-2, item (57) delete "and phosph (on) atacetal compounds," and insert -- and phosph(on)atacetal compounds, --.

Column 1, Page 2, Line 42, delete "WO WO 14/074725 5/2014 WO WO 1234567 6/2014" and insert -- WO WO 14/074725 5/2014 --.

In the Specification

Column 11, Line 63, delete "and amidases" and insert -- and amidases. --.

Column 12, Line 38, delete "and V have" and insert -- and VI have --.

Column 12, Line 42, delete "I, I, III," and insert -- I, II, III, --.

Column 15, Line 37, delete "nitro, 0-carbamyl, N-carbamyl," and insert -- nitro, O-carbamyl, N-carbamyl, --.

Column 15, Line 55, delete "a "—C(=)OR" group" and insert -- a "—C(=O)OR" group --.

Column 16, Line 19, delete "which R and" and insert -- which $R_A$ and --.

Column 16, Line 23-24, delete "an "—N($R_A$)C(=O)ORB" group" and insert -- an "—N($R_A$)C(=O)O$R_B$" group --.

Column 16, Line 33-34, delete "an "—N($R_A$)C(=S)ORB" group" and insert -- an

Signed and Sealed this
Fourth Day of February, 2025

Coke Morgan Stewart
*Acting Director of the United States Patent and Trademark Office*

"—N(R$_A$)C(=S)OR$_B$" group --.

Column 16, Line 62, delete "alkenyl, C$_{2-4}$ alkynyl," and insert -- alkenyl, C$_{2-6}$ alkynyl, --.

Column 18, Line 67, delete "—CH$_2$CH$_2$—, —CH$_2$CH(CH)CH$_2$—, and" and insert -- —CH$_2$CH$_2$—, —CH$_2$CH(CH$_3$)CH$_2$—, and --.

Column 19, Line 9, delete "is resent:" and insert -- is present: --.

Column 20, Line 11, delete "the leftnost attachment" and insert -- the leftmost attachment --.

Column 21, Line 17 (approx.), delete "HOOC-, HOOPR$_2$-, associated" and insert -- HOOC-, HOOPR2-, associated --.

Column 23, Line 57 (approx.), delete "Emitricitabine" and insert -- Emtricitabine --.

Column 29, Line 24-25, delete "HCl (IM), NaHCO$_3$(saturated), and" and insert -- HCl (1M), NaHCO$_3$ (saturated), and --.

Column 31, Line 7 (approx.), delete "(Compound 104" and insert -- (Compound 104) --.

Column 31, Line 33 (approx.), delete "for C$_2$H$_{35}$FN$_3$O$_9$P: 572.22;" and insert -- for C$_{25}$H$_{35}$FN$_3$O$_9$P: 572.22; --.

Column 31, Line 39, delete "amino)phenoxy)" and insert -- amino)(phenoxy) --.

Column 32, Line 5, delete "amino)phenoxy)" and insert -- amino)(phenoxy) --.

Column 33, Line 5 (approx.), delete "amino)phenoxy)" and insert -- amino)(phenoxy) --.

Column 36, Line 11, delete "3-ylpropionate (Compound" and insert -- 3-yl propionate (Compound" --.

Column 36, Line 18-32, delete " 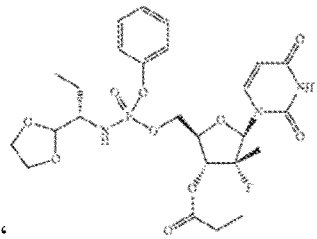 " and insert

CERTIFICATE OF CORRECTION (continued)
U.S. Pat. No. 12,110,308 B2

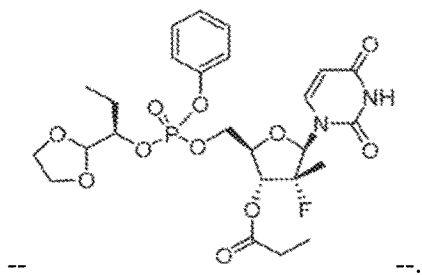
--.

Column 36, Line 66, delete "for $C_{25}H_{32}FN_2O_{10}P$: 587.18;" and insert -- for $C_{25}H_{32}FN_2O_{11}P$: 587.18; --.

Column 37, Line 63, delete "Compound 11 was" and insert -- Compound 116 was --.

Column 40, Line 67, delete "for $C_{22}H_{31}N_6OP$: 491.22;" and insert -- for $C_{22}H_{31}N_6O_5P$: 491.22; --.

Column 41, Line 28, delete "for $C_{26}H_{35}N_6O_5P$: 539.22;" and insert -- for $C_{26}H_{31}N_6O_5P$: 539.22; --.

Column 42, Line 67, delete "found: 505.2" and insert -- found: 505.2. --.

Column 43, Line 44-53 (approx.), delete " 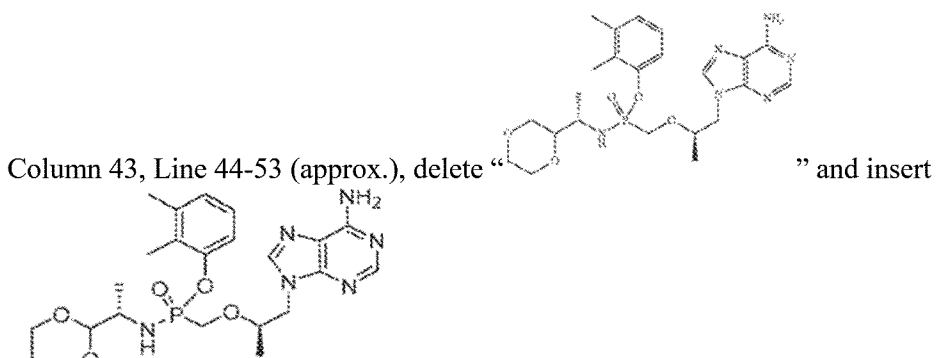 " and insert
--  --.

Column 45, Line 35, delete "(Compound 133B" and insert -- (Compound 133B) --.

Column 47, Line 24, delete "Compound was" and insert -- Compound 136 was --.

Column 47, Line 67, delete "found: 493.2" and insert -- found: 493.2. --.

Column 49, Line 35 (approx.), delete "(phenoxyphosphoryl)" and insert -- (phenoxy)phosphoryl) --.

Column 51, Line 37 (approx.), delete "(Compound 45)" and insert -- (Compound 145) --.

Column 54, Line 27, delete "fluoro-((2R" and insert -- fluoro-1-((2R --.

Column 54, Line 64, delete "fluoro-((2R" and insert -- fluoro-1-((2R --.

Column 55, Line 27 (approx.), delete "fluoro-((2R" and insert -- fluoro-1-((2R --.

Column 57, Line 67, delete "for $C_{25}H_{35}FN_3O_1O_5P$: 586.19;" and insert -- for $C_{25}H_{35}FN_3O_{10}P$:

586.19; --.

Column 58, Line 28, delete "fluoro-((2R" and insert -- fluoro-1-((2R --.